Figure 1:
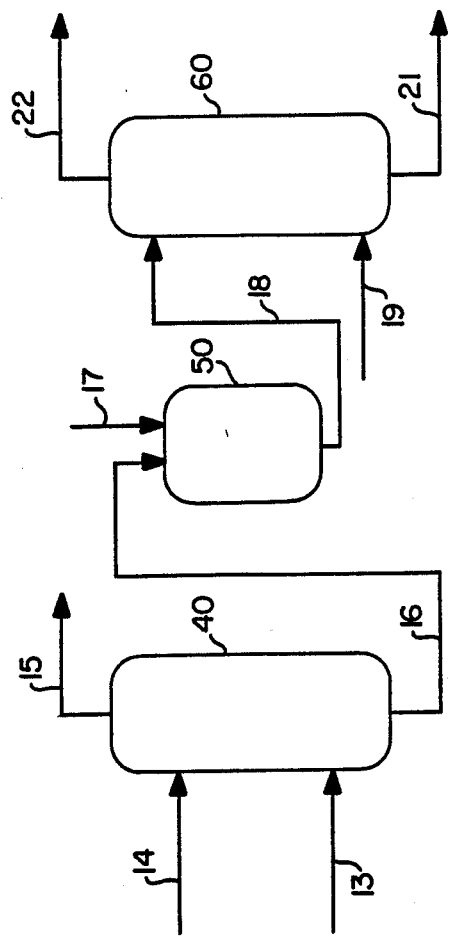
Figure 2:
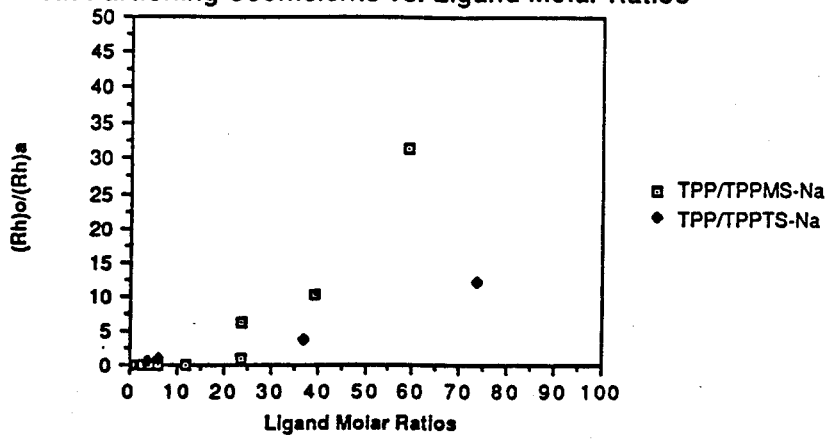
Figure 3:
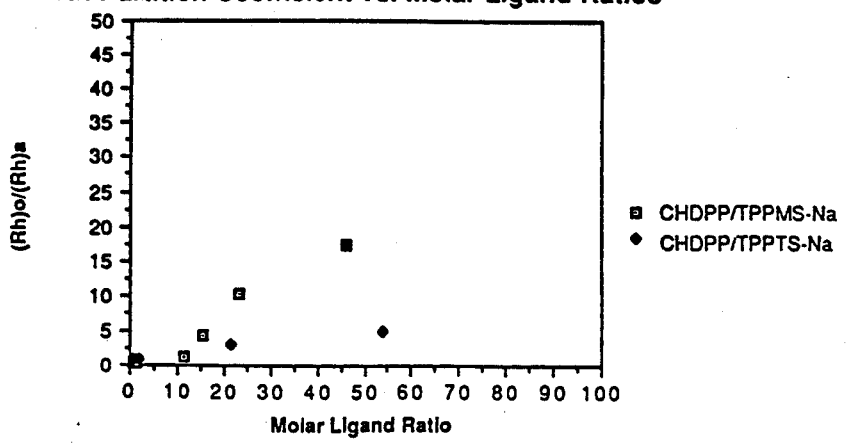
Figure 4:
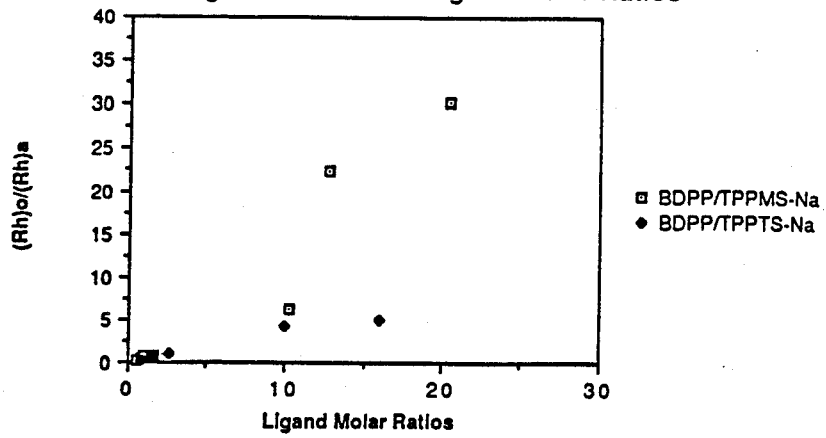
Figure 5:
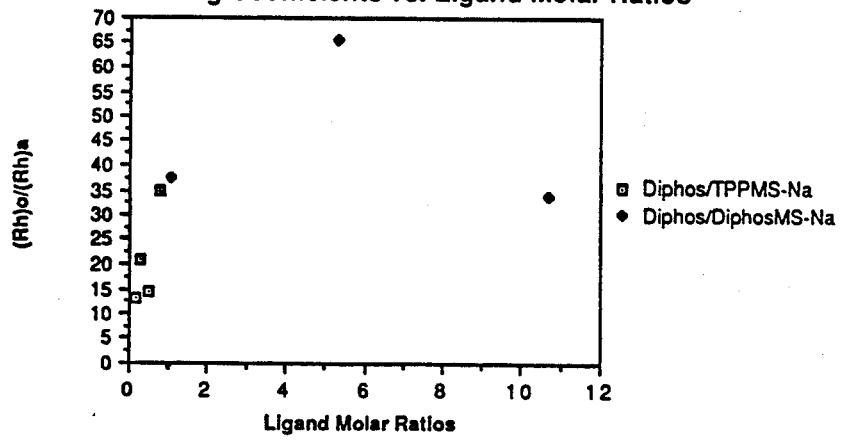

United States Patent [19]

Miller et al.

[11] Patent Number: 4,935,550
[45] Date of Patent: Jun. 19, 1990

[54] CATALYTIC METAL RECOVERY FROM NON-POLAR ORGANIC SOLUTIONS

[75] Inventors: David J. Miller, Charleston; David R. Bryant, South Charleston, both of W. Va.

[73] Assignee: Union Carbide Chemicals and Plastics Company Inc., Danbury, Conn.

[21] Appl. No.: 231,508

[22] Filed: Aug. 12, 1988

[51] Int. Cl.⁵ .................. C07C 45/50; C07C 45/78
[52] U.S. Cl. ...................... 568/454; 502/24; 502/30; 568/492
[58] Field of Search .............. 568/454, 492; 502/24, 502/30

[56] References Cited

U.S. PATENT DOCUMENTS

| | | | |
|---|---|---|---|
| 3,968,134 | 7/1976 | Gregorio et al. | 568/454 |
| 4,242,284 | 12/1980 | Harris et al. | 568/454 |
| 4,248,802 | 2/1981 | Kuntz | 568/454 |
| 4,283,304 | 8/1981 | Bryant et al. | 568/454 |
| 4,292,196 | 9/1981 | Homeier et al. | 568/454 |
| 4,297,239 | 10/1981 | Bryant et al. | 568/454 |
| 4,364,907 | 12/1982 | Barnes | 568/454 |
| 4,374,278 | 2/1983 | Bryant et al. | 568/454 |
| 4,399,312 | 8/1983 | Russell et al. | 568/454 |
| 4,473,655 | 9/1984 | Tsunda et al. | 568/454 |
| 4,504,588 | 3/1985 | Gartner et al. | 568/454 |
| 4,537,997 | 9/1985 | Kojima et al. | 568/454 |
| 4,568,653 | 2/1986 | Schwirten et al. | 568/454 |
| 4,633,021 | 12/1986 | Hanes | 568/454 |

FOREIGN PATENT DOCUMENTS

| | | | |
|---|---|---|---|
| 147824 | 12/1984 | European Pat. Off. | 568/454 |
| 3411034 | 9/1985 | Fed. Rep. of Germany | 568/492 |
| 3443474 | 5/1986 | Fed. Rep. of Germany . | |

*Primary Examiner*—Werren B. Lone
*Attorney, Agent, or Firm*—Reynold J. Finnegan

[57] ABSTRACT

A method for recovering a transition metal, e.g., rhodium, from a non-polar organic solution containing non-polar organic solvent-soluble and polar solvent-insoluble coordination complex of the transition metal and a non-polar organic solvent-soluble and polar solvent-insoluble ligand, e.g., an organophosphorus ligand, by contacting the non-polar organic solution with a polar solution of an ionic organophosphine ligand, the transition metal then can be transferred back into a non-polar solution for reuse. In one embodiment rhodium is rendered amenable for back-extraction by treating the polar solution with a suitable conditioning reagent.

29 Claims, 3 Drawing Sheets

CATALYTIC METAL RECOVERY FROM NON-POLAR ORGANIC SOLUTIONS

BACKGROUND OF THE INVENTION

1. Field of the Invention

This invention broadly relates to a method for recovering for subsequent use Group VIII transition metals from a non-polar organic solution containing a coordination complex a Group VIII transition metal and an organo-substituted ligand of a trivalent atom of a Group VA element including phosphorus, arsenic and antimony, e.g., an organophosphorus ligand. This invention particularly relates to a method for recovering rhodium from a solution of a rhodium-organophosphorus ligand coordination complex in a non-polar solvent used in the hydroformylation of olefinic compounds.

2. Description of Related Art

Processes using transition metal-ligand complexes as homogeneous catalysts are well-known. Included in such processes are the hydrogenation of unsaturated compounds, the carbonylation of methanol to acetic acid, olefin dimerization and oligomerization processes, the hydrocyanation of butadiene to adiponitrile and olefin hydrosilylation reactions. Still other processes are known to those skilled in the art. Oftentimes, recovery of the transition metal from the catalyst solutions used in these process presents a particularly troublesome problem.

Particularly illustrative of these homogeneous catalysis systems is the hydroformylation of olefinic compounds with carbon monoxide and hydrogen to produce aldehydes in the presence of a coordination complex of a Group VIII transition metal and an organophosphorus ligand dissolved in an organic (non-polar) solvent. U.S. Pat. No. 3,527,809, for example, teaches selectively hydroformylating alphaolefins with certain rhodium-triorganophosphine and triorganophosphite ligand catalyst complexes to produce oxygenated products rich in normal aldehydes. U.S. Pat. Nos. 4,148,830 and 4,247,486 disclose hydroformylation processes which use rhodium triarylphosphine ligand catalyst complexes. U.S. Pat. No. 4,283,562 discloses that branched-alkyl-phenylphosphine or cycloalkylphenylphosphine ligands can be employed in a rhodium catalyzed hydroformylation process in order to provide a more stable catalyst. U.S. Pat. No. 4,400,548 discloses that bisphosphine monoxide ligands can be employed for hydroformylation and such ligands provide rhodium catalyst complexes of improved thermal stability. Other patents describing hydroformylation processes and catalysts include U.S. Pat. Nos. 4,599,206; 4,668,651; 4,717,775; 4,737,588; and 4,748,261.

Rhodium complex catalyzed hydroformylation processes preferably are carried out in a non-aqueous hydroformylation reaction medium containing an organic (non-polar) solvent and both organic solvent-soluble catalyst complex and soluble free ligand, i.e., ligand not tied to or bound to the rhodium catalyst complex. Organic (non-polar) solvents which do not interfere with the hydroformylation process can be employed. Included in the group of suitable non-polar organic solvents are compounds belonging to the general classes of alkanes, ethers, aldehydes, ketones, esters, amides, and aromatics.

Aldehyde compounds corresponding to the desired aldehyde products and especially higher boiling liquid aldehyde condensation by-products (oligomers) produced in situ during the hydroformylation process are particularly useful as non-polar organic solvents in rhodium-catalyzed hydroformylation. In this regard, the aldehyde product and the corresponding aldehyde trimers are preferred for start-up of a continuous hydroformylation process. However, as hydroformylation proceeds, the solvent typically will comprise both aldehyde products and higher boiling liquid aldehyde condensation by-products due to the nature of such continuous processes. Methods for the preparation of such aldehyde condensation by-products are more fully described in U.S. Pat. Nos. 4,148,830 and 4,247,486.

It may be preferred to separate and recover the desired aldehyde product from the non-polar hydroformylation reaction medium containing the catalyst complex by vaporization or distillation. Hydroformylation systems using both continuous gas recycle and liquid recycle are known. In a continuous liquid catalyst recycle operation such as described in U.S. Pat. No. 4,148,830, liquid aldehyde condensation by-products including aldehyde trimers and higher oligomers, produced under hydroformylation conditions from the desired aldehyde product, are employed as the reaction solvent for the catalyst. This process has been used widely to hydroformylate lower olefinic compounds containing from two to five carbon atoms, particularly lower alpha-olefins, to produce aldehydes containing from three to six carbon atoms. In general, it is preferred to separate the desired aldehyde product from the rhodium containing product solution by selective vaporization of the aldehyde under reduced pressure and at temperatures below about 150° C., preferably below about 130° C.

Commercial experience has shown that the rhodium catalyst complexes used in hydroformylating olefinic compounds are deactivated by the presence in the feedstock of extrinsic catalyst poisons, such as sulphurous compounds (e.g. $H_2S$, COS and $CH_3SH$) or halogen compounds (e.g. HCl), which can react with the rhodium of the catalyst to form inactive species which are not destroyed under the mild hydroformylation conditions employed. Hence great care is taken to purify the various feedstocks. Deactivation of the rhodium hydroformylation catalyst also occurs, however, even in the substantial absence of extrinsic poisons. This deactivation is referred to as intrinsic deactivation and is believed to be due, inter alia, to the effects of temperature, reactant partial pressures, specific organophosphorus ligands employed, and the rhodium concentration. The extent of catalyst deactivation (or the catalyst activity) is determined at any particular time by comparing the conversion rate of reactants to aldehyde product at that particular time, to the conversion rate obtained using fresh catalyst.

Another potential problem for continuous hydroformylation processes is the accumulation of aldehyde condensation by-products of low volatility relative to the organophosphorus ligand. Since commercial processes rely on vaporization or distillation to separate the reaction product medium containing the rhodium-ligand complex from the desireed aldehyde hydroformylation products, the accumulation of high boiling aldehyde condensation by-products having a low volatility must be accounted for when designing the hydroformylation process.

When continiuously hydroformylating lower olefinic compounds, the accumulation rate of high boiling aldehyde condensation by-products normally is sufficiently low that it can be easily controlled. Thus, in the case of hydroformylating lower olefins, catalyst life mainly is limited by the rate of catalyst deactivation. In present commercial plants, it is not unusual to operate the process for upwards of one year or more during which time any decline in catalyst activity or catalyst loss may be easily offset by addition of fresh catalyst or catalyst precursor, together with fresh organophosphorus ligand if desired. However, in such systems when the level of deactivated rhodium species rises to undesirable values and it is no longer considered economical to continue the hydroformylation process, it may become expedient simply to replace the catalyst charge completely, even though it may still contain a significant proportion of active rhodium catalyst complex. Because rhodium is and expensive metal, however, it is uneconomical to discard the spent catalyst and a usual practice is for the catalyst to be reactivated. U.S. Pat. Nos. 4,297,239; 4,374,278 and 4,446,074, for example, describe procedures for reprocessing and reactivating spent hydroformylation catalyst.

Continuous hydroformylation of higher olefinic compounds, such as higher alpha-olefins, containing six or more carbon atoms, e.g., from six to thirty carbon atoms, using conventional organic (non-polar) solvent-solubilized organophosphorus ligands, involves a further problem since aldehyde condensation by-products, having a low volatility relative to the organophosphorus ligands, accumulate at a much higher rate than encountered during the hydroformylation of lower olefins. Unfortunately the high rate of accumulation of such high boiling aldehyde condensation by-products cannot be readily controlled by removing same by distillation from the catalyst solution during the hydroformylaton without incurring significant energy costs and exposing the catalyst to severe temperature conditions. Thus, it may be more practical to let such hydroformylations of higher olefins to merely run their course until the accumulation of such by-products becomes so great as to overwhelm the catalyst solution and economically prevent its further usefulness, at which time the catalyst solution needs to be replaced with a fresh catalyst solution.

There remains, however, the additional problem of recovering the rhodium values, much of which may still be highly active, from said overwhelmed catalyst solution that is replaced. In fact, the hydroformylation catalyst still may exhibit over 75% and possibly even over 90% of its initial catalytic activity at this time. Again, unfortunately, due to their low volatility, the removal of such by-products from the replaced hydroformylation catalyst solution using conventional distillation techniques is plagued by the same energy-related and thermal exposure problems referenced above. Thus, there is a need in the art for a less energy intensive method for recovering rhodium from such catalyst solutions under more mild temperature conditions than possible using distillation procedures.

Thus, it is an object of the present invention to provide a method for recovering Group VIII transition metals and particularly rhodium from substantially non-polar organic solutions containing coordination complexes of the transition metals and organo-substituted ligands of a trivalent atom of a Group VA element such as organophosphorus ligands. Such a method potentially has application in the wide variety of homogeneous catalysis applications noted earlier, and particularly for removing rhodium from substantially non-polar organic solutions in which large concentrations of hard-to-remove components have accumulated, such as the high boiling aldehyde condensation by-products that accumulate during the hydroformylation of higher olefinic compounds.

BRIEF DESCRPTION OF THE DRAWINGS

FIG. 1 schematically illustrates a flow sheet of a recovery process of the present invention.

FIGS. 2 through 5 graphically illustrate the results of Example 32 by plotting petitioning coefficient between non-polar (O) and polar (A) phases as a function of the ratio of the ligand molar concentration in the non-polar and polar phases.

DISCLOSURE OF THE INVENTION

In one aspect, the present invention is directed broadly to a method for recovering Group VIII transition metal from a substantially non-polar organic solution containing a non-polar organic solvent-soluble and polar solvent-insoluble coordination complex of a Group VIII transition metal and an organo-substituted ligand of a trivalent atom. The method comprises contacting the non-polar organic solution with a polar solution containing a polar solvent-soluble organo-substituted ligand of a trivalent atom capable of forming a coordination complex with the transition metal and transferring said Group VIII transition metal from said non-polar organic solution into said polar solution.

In an additional aspect, the invention broadly pertains to a method for extracting Group VIII transition metal from a substantially non-polar organic solution into a polar solution containing polar solvent-soluble organo-substituted ligand of a trivalent atom and thereafter transferring the Group VIII transition metal from the polar solution back into a non-polar organic solvent containing a non-polar organic solvent-soluble and polar solvent-insoluble organo-substituted ligand of a trivalent atom, also capable of forming a coordination complex with the transition metal.

The present invention is based on the discovery that a substantially non-polar organic solution of a coordination complex of a Group VIII transition metal and an organo-substituted ligand of a trivalent Group VA element (also referred to herein simply as "an organo-substituted trivalent ligand"), which also may contain a large amount of free organo-substituted ligand, can be contacted with a polar solvent selected from the group consisting of water, methanol and mixtures thereof having dissolved therein an organo-substituted ligand capable of forming a complex with the Group VIII transition metal to transfer (i.e., extract) the transition metal from the substantially non-polar organic solution into the polar solvent (solution). Although not wishing to be bound by any particular explanation, it is believed that the non-polar organic solvent-soluble and polar solvent-insoluble transition metal-ligand complex is converted into a polar solvent-soluble transition metal-ligand complex during contact between the non-polar and polar solutions and thus the transition metal is extracted in the form of a polar solvent-soluble coordination complex. It is particularly surprising that transport of transition metal can be obtained from a non-polar organic solution that contains both ligand in complex coordination with the transition metal and a large amount of free ligand using as the extractant a different solution containing only a small amount of a different ligand.

The present invention has broad applicability to the recovery of Group VIII transition metals, such as cobalt, nickel, rhodium, palladium, ruthenium, platinum and the like, from substantially non-polar organic solutions containing coordination complexes of such metals, as for example may be used inter alia in hydrogenating unsaturated compounds, such as in the hydrogenation of copolymers of a conjugated diene and co-polymerizable monomers as described in U.S. Pat. Nos. 4,464,515 and 4,503,196, in carbonylating methanol to acetic acid, in oligomerizing olefins, in hydrocyanating butadiene to adiponitrile, in decarbonylating aldehydes and in hydrosilylating olefins. For convenience in presentation, however, the invention will be described hereinafter with specific reference to the recovery of rhodium from substantially non-polar organic solutions of rhodium-organophosphorus ligand complexes used, for example, in hydroformylating olefinic compounds. The broad applicability of the present invention will nonetheless be appreciated and understood by those skilled in the art.

In a similar vein, while the non-polar organic solvent-soluble and polar solvent-insoluble ligand broadly can be organophosphorus compound, an organoarsenic compound, or an organoantimony compound, the invention will be described with specific reference to the use of organophosphorus ligands such as organophosphines, organophosphites and the like, as will be apparent from the subsequent disclosure. Those skilled in the art however will recognize the broad applicability of the present invention in view of the following description and specific examples.

In this context, therefore, the invention particularly relates to a method for recovering rhodium from a substantially non-polar organic solution that contains non-polar organic solvent-soluble and polar solvent-insoluble coordination complex of rhodium and an organophosphorus ligand comprising:

(a) contacting said organic solution with a polar solution containing polar solvent-soluble, ionic organophosphine ligand capable of forming a coordination complex with the rhodium to transfer rhodium from said non-polar organic solution into the polar solution; and (b) transferring the rhodium from said polar solution into a non-polar organic solvent containing non-polar organic-soluble and polar solvent-insoluble organophosphorus ligand capable of forming a coordination complex with the rhodium.

In one embodiment, the polar solution containing said transferred rhodium is treated with a conditioning reagent to reduce the amount of polar solvent-soluble ionic organophosphine ligand capable of forming a coordination complex with rhodium in said polar solution; and the polar solution so-produced is contacted with a non-polar organic solvent containing non-polar organic solvent-soluble and polar solvent-insoluble organophosphorus ligand capable of forming a coordination complex with rhodium to transfer rhodium from said polar solution into the non-polar organic solvent.

In yet another aspect, the present invention relates to an improvement in a continuous process for hydroformylating olefinic compounds of six to thirty carbon atoms in a hydroformylation reactor to form aldehydes by reacting the olefinic compound with hydrogen and carbon monoxide in the presence of a non-polar hydroformylation reaction medium comprising a non-polar organic solution of a catalytic amount of a non-polar organic solvent-soluble and polar solvent-insoluble, rhodium-organophosphorus ligand coordination complex, and free non-polar organic solvent-soluble and polar solvent-insoluble organophosphorus ligand, said improvement comprising;

(a) contacting all or part of said hydroformylation reaction medium, after its removal from the hydroformylation reactor, with a polar solution containing polar solvent-soluble ionic organophosphine ligand capable of forming a coordination complex with rhodium to transfer rhodium from said hydroformylation reaction medium into the polar solution;

(b) subsequently transferring the rhodium from said polar solution into a non-polar organic solvent containing non-polar organic-soluble and polar solvent-insoluble organophosphorus ligand capable of forming a coordination complex with the rhodium, and (c) adding the non-polar organic solvent containing said transferred rhodium to the hydroformylation reaction medium of said hydroformylation reactor.

If desired, the rhodium in the polar solution can be transferred to a non-polar organic solvent after first treating the polar solution with a conditioning reagent followed by back-extraction with the non-polar organic solvent.

Throughout the specification and claims the phrases "non-polar" solvents, "non-polar" solutions, "non-polar" hydroformylation reaction medium, and the like are used to describe organic solvents, organic solutions and organic reaction mediums that are essentially immiscible with water, methanol, mixtures thereof, and solutions made therefrom. Conversely, the phrases "polar" solvent, "polar" solution, and the like, used throughout the specification and claims, refer to water, methanol, mixtures thereof and solutions made therefrom.

The terms "organic solution", "hydroformylation reaction medium" and the like, are used to describe substantially non-polar liquid compositions, or any part thereof, containing a non-polar organic solvent, a non-polar organic solvent-soluble and polar solvent-insoluble rhodium-organophosphorus ligand coordination complex and preferably free non-polar organic solvent-soluble and polar solvent-insoluble organophosphorus ligand, such as may be recovered from a process directed to producing aldehydes by hydroformylating an olefinic compound with carbon monoxide and hydrogen in the presence of an organic solution of the coordination complex catalyst.

Of course it should be understood that such organic solutions, and hydroformylation reaction mediums in particular, can contain additional constituents, e.g., which have either been deliberately employed in the hydroformylation process or which are formed in situ during said process. Examples of such constituents that generally will also be present in a hydroformylation process include free non-polar organic solvent-soluble organophosphorus ligand, unreacted olefinic starting material, dissolved carbon monoxide and hydrogen gases, aldehyde product, and in situ formed by-products, such as saturated hydrocarbons and unreacted isomerized olefins corresponding to the olefin starting materials, and high boiling liquid aldehyde condensation by-products, and the like.

As indicated above, methods for hydroformylating olefinic compounds to produce aldehydes using a substantially non-polar reaction medium comprising an organic solution of a rhodium-organophosphorus ligand coordination complex catalyst and free organophosphorus ligand, using for example a triarylphosphine ligand, are well known in the art. The present invention does not depend upon the particular hydroformylation process used, the reaction conditions or ingredients employed in the hydroformylation process, or the exact structure of the transition metal-coordination complex species, which may be present in mononuclear, dinuclear, and polynuclear forms. Indeed, the exact active catalyst structure is not known with certainty.

Thus, the present invention can be used to recover rhodium from any of the wide variety of non-polar organic solutions containing rhodium-ligand coordination complexes used, for example, in hydroformylation processes. Such organic solutions can contain any of the wide variiety of non-polar organic solvent-soluble and polar solvent-insoluble organophosphorus ligands generally present in such compositions both as part of a coordination complex with a transition metal, i.e. rhodium, and in free form.

Illustrative non-polar organic solvent-soluble and polar solvent-insoluble organophosphorus ligands that may be employable in this invention include, e.g., trialkylphosphines and phosphites, dialkylphosphines and phosphites, alkyldiarylphosphines and phosphites, triaralkylphosphines and phosphites, dicycloalkylarylphosphines and phosphites, cycloalkyldiarylphosphines and phosphites, tricycloalkylphosphines and phosphites, triarylphosphines and phosphites, alkyl and/or aryl bisphosphines and bisphosphine mono-oxides, diorganophosphites, organobisphosphites and polyphosphites, and the like. Mixtures of such ligands, as well as tertiary organophosphinite ligands, may also be employed if desired.

Such organophosphines and organophosphites and/or methods for their preparation are well known in the art as described e.g. in U.S. Pat. Nos. 3,527,809; 4,148,830; 4,247,486; 4,260,828; 4,283,562; 4,306,087; 4,400,548; 4,429,161; 4,482,749; 4,491,675; 4,528,403; 4,593,011; 4,593,127; 4,599,206; 4,668,651; 4,694,109; 4,717,775; 4,748,261 European Patent Applications Publication Nos. 96,986; 96,987; and 96,988 (all published Dec. 28, 1983); PCT Applications Publication Nos. WO 80/01690 (published Aug. 21, 1980) and WO 87/07600 (published Dec. 17, 1987); and the like, the entire disclosures of which are incorporated herein by reference thereto. Of course the hydrocarbon radicals of such organophosphorus ligands may be substituted if desired, with any suitable substituent that does not unduly adversely affect the desired result of the hydroformylation process or this invention. Illustrative substituents that may be on the hydrocarbon radicals in addition of course to corresponding hydrocarbon radicals such as alkyl, aryl, aralkyl, alkaryl and cyclohexyl substituents, may include for example silyl radicals; amino radicals; acyl radicals: acyloxy radicals; amido radicals; sulfonyl radicals; alkoxy radicals; thionyl radicals; phosphonyl radicals: as well as, halogen, nitro, cyano, trifluoromethyl, and hydroxy radicals, and the like, such as disclosed e.g. in U.S. Pat. Nos. 3,527,809 and 4,717,775. Of course it is to be understood that any substituted or unsubstituted hydrocarbon groups that make up a particular given organophosphorus ligand may be the same or different.

Preferred organophosphines include the tertiary organophosphines mentioned above, especially triphenylphosphine, propyldiphenylphosphine, t-butyldiphenylphosphine, n-hexyldiphenylphosphine, cyclohexyldiphenylphosphine, dicyclohexylphenylphosphine, tricyclohexylphosphine, tribenzylphosphine, and the like.

Preferred organophosphites include triarylphosphites e.g. triphenylphosphite as well as diorganophosphites such as disclosed e.g. in U.S. Pat. No. 4,717,775, organobisphosphites such as disclosed e.g. in U.S. Pat. No. 4,749,261 and organobis- and polyphophites such as disclosed e.g. in U.S. Pat. No. 4,668,651.

Of course it is to be understood that the term "complex catalyst," "coordination complex" and the like means a coordination compound formed by the union of one or more electronically rich molecules or atoms capable of independent existence, with one or more electronically poor molecules or atoms each of which also is capable of independent existence. Organophosphorus ligands, whose phosphorus atom (or other hereto-atom such as oxygen) has one available or unshared pair of electrons, are capable of forming a coordinate bond with Group VIII transition metals such as rhodium. The ultimate composition of the coordination complex also may contain additional ligands which satisfy the coordination sites or nuclear charge of the complex such as carbon monoxide, hydrogen and the like.

As pointed out in the identified prior art, the rhodium coordination complex employed in hydroformylation reactions as the complex catalyst may be formed initially by methods known in the art. For example, a performed stable crystalline solid or rhodium hydridocarbonyl-tris (triphenylphosphine), may be introduced into the reaction medium of a hydroformylation process. Such a material may be formed for example, by a method disclosed in Brown et. al. *Journal of the Chemical Society*, 1970, pages 2753-2764.

Alternatively, the rhodium coordination complex catalyst present in the hydroformylation reaction medium can be derived initially from a rhodium catalyst precursor such as rhodium carbonyl triorganophosphorus (e.g. triphenyl) acetylacetonate, $Rh_2O_3$, $Rh(OAc)_3$, $Rh_4(CO)_{12}$, $Rh_6(CO)_{16}$, $Rh(NO_3)_3$ or rhodium dicarbonyl acetylacetonate, and the like, which have been introduced into the reaction medium of a hydroformylation process and form, in situ, e.g. rhodium coordination complex catalyst consisting essentially of carbon monoxide and organophosphorus ligands. The terminology "consisting essentially of" when used herein in connection with a hydroformylation catalyst is not meant to exclude, but rather include, hydrogen as well as carbon monoxide and organophosphorus complexed with the rhodium, said hydrogen and carbon monoxide of course being derived from the hydrogen and carbon monoxide gases which are an integral part of any hydroformylation process if not already present in the catalyst precursor. It is not intended to limit the present invention by the above explanation as to which organophosphorus ligand (or relative amount thereof) is tied to or complexed with the rhodium, nor as to the relative proportions of free organophosphorus ligand. Rhodium coordination complex obtained upon transferring rhodium, from the polar solution initially used to remove rhodium from hydroformylation reaction medium back into a non-polar organic solution containing an organophosphorus ligand, in accordance with the present invention, also forms an active rhodium coordination complex in the hydroformylation reaction medium under the conditions of hydroformylation.

The present invention has particular applicability for treating a hydroformylation reaction medium from processes used to hydroformylate higher olefins containing from six to thirty carbon atoms. A process suitable for hydroformylating such higher olefinic compounds is described in U.S. Pat. No. 4,593,127 and uses a substantially non-polar hydroformylation reaction medium comprising both the non-polar organic solvent-soluble and polar solvent-insoluble rhodium-organophosphorus ligand coordination complex catalyst and free non-polar organic solvent-soluble and polar solvent-insoluble organophosphorus ligand dissolved in a non-polar organic solvent. By "free ligand" is meant organophosphorus ligand that has not formed a complex with the rhodium.

The olefinic hydrocarbon reactant together with carbon monoxide and hydrogen are fed into a hydroformylation reactor containing the hydroformylation catalyst. Suitable olefinic compounds can be terminally or internally unsaturated and can have straight-chain, branched-chain or cyclic structures and can also be a mixture of olefin, such as obtained from the oligomerization of propene, butene, isobutene, etc., (such as so called dimeric, trimeric or tetrameric propylene, codibutylene, and the like, as disclosed e.g. in U.S. Pat. Nos. 4,518,809 and 4,528,403). Moreover, such olefinic compounds may further contain one or more ethylenic unsaturated groups and of ocurse mixtures of two or more different olefinic compounds may be employed as the starting hydroformylation material if desired. Further such olefinic compounds and the corresponding aldehyde products derived there from may also contain one or more groups or substituents which do not unduly adversely affect the hydroformylation process or the process of this invention such as carbonyl, carbonyloxy, oxy, hydroxy, oxycarbonyl, halogen, alkoxy, aryl, haloalkyl, and the like as described e.g. in U.S. Pat. Nos. 3,527,809 and 4,731,486.

Illustrative olefinic unsaturated compounds are alpha-olefins, internal olefins, alkyl alkenoates, alkenyl alkanoates, alkenyl alkyl ethers, alkenols, and the like e.g., ethylene, propylene, 1-butene, 1-hexene, 1-heptene, 1-octene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-pentene, 2-hexene, 2-heptene, propylene dimers, propylene trimers, propylene tetramers, 2-ethyl hexene, 2-octene, styrene, 3-phenyl-1-propene, 1,4-hexadiene, 1,7-octadiene, 3-cyclohexyl-1-butene, allyl butyrate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-disopropenyl-benzene, eugenol, iso-eugenol, salfrole, iso-safrole, anethol, 4-allylanisole, indene, limonene, beta-pinene, dicyclopentadiene, cyclooctadiene, camphene, linalool, and the like.

As noted above, the hydroformylation reaction medium consists essentially of a non-polar organic solvent-soluble and polar solvent-insoluble coordination complex of rhodium and an organophosphorus ligand and free organophosphorus ligand both dissolved in a non-polar organic solvent. Any non-polar organic solvent which does not adversely affect the desired hydroformylation reaction can be employed, especially including those solvents known to be suitable for use in prior art hydroformylation processes as previously described. In accordance with the present invention, the non-polar organic solvent employed must be sufficiently immiscible with a polar solution so that the hydroformylation reaction medium forms a distinct non-polar liquid phase in the presence of the polar phase. The non-polar organic solvent also preferably exhibits very little solubility in the polar solution so as to minimize any added costs associated with recovery and/or replacement of the various constituents of the polar and non-polar phases.

The amount of non-polar organic solvent is not critical and need only be that amount which provides the desired rhodium and dissolved ligand concentrations. Typically, the amount of organic solvent may range from about 5 percent by weight up to about 95 percent by weight or more based on the total weight of the hydroformylation reaction medium.

Hydroformylation is effected in the liquid reaction medium (non-polar organic solution) in the presence of a catalytically effective amount of non-polar organic solvent-soluble and polar solvent-insoluble rhodium-organophosphorus ligand coordination complex. The rhodium complex concentration may range from about 1 part per million (ppm), calculated as rhodium metal, up to about 50,000 parts per million (ppm), or more, with a rhodium concentration in the range of about 10 ppm to 1,500 ppm being sufficient for most hydroformylations. Generally, there is no advantage to the hydroformylation reaction in using concentrations of rhodium in excess of about 1,000 ppm. Usually, on the grounds of expense alone, it will be preferred to operate at an active rhodium coordination complex catalyst concentration of not more than about 500 ppm, calculated as rhodium metal, while more typical operating conditions generally utilize active rhodium coordination complex catalyst concentrations of from about 50 ppm up to about 350 ppm, calculated as rhodium metal.

The liquid hydroformylation reaction medium also preferably contains free non-polar organic solvent-soluble and polar solvent-insoluble ligand. Thus, preferably there are at least about 1 mol of free ligand for every gran-atom (mol) of rhodium present. Usually it will be preffered to operate in the presence of at least 2 mols of free ligand. In the case where triphenylphosphine (TPP) ligand is used, it is preferred to operate the hydroformylation reaction in the presence of at least about 75 mols, and more preferably at least about 100 mols, of free organophosphorus ligand per gram-atom of rhodium. Other organophosphorus ligands, e.g. cyclohexyldiphenylphosphine and diorganophosphites, are preferably employed in less amounts, such as e.g. from about 3 to 50 mols of ligand per mol of rhodium. Thus, the upper limit of the amount of free organophosphorus ligand is not particularly critical and is dictated mainly by the particular organophosphorus ligand employed, by the solubility thereof in the non-polar reaction medium, as well of course by economic and commercial considerations.

The conditions for effecting the hydroformylation reaction process are not critical to the present invention since said process serves only as a means for preferably furnishing the non-polar organic solution starting material of this invention. Accordingly, such conditions may be those heretofore conventionally used, i.e., a reaction temperature of from about 45° C. to about 200° C. and pressures ranging from about 1 to 10,000 psia. While optimization of reaction conditions to achieve best results and the desired efficiency is dependent upon one's experience in hydroformylation, only routine experimentation should be necessary to determine conditions optimum for a given situation. Such experimentation is well within the knowledge of one skilled in the art.

For instance, the total gas pressure of hydrogen and carbon monoxide starting materials for the hydroformylation process may range from about 1 to about 10,000 psia. It is generally preferred that the process be operated at a total gas pressure of hydrogen and carbon monoxide of less than about 1500 psia, and more preferably less than about 500 psia. The minimum total pressure of the gaseous reactants is not critical and is limited only by the quantity of reactants necessary to obtain a desired rate of reaction. More specifically, a carbon monoxide partial pressure in the hydroformylation process of from about 1 to about 120 psia generally is preferred, more preferably from about 3 to about 90 psia, while the hydrogen partial pressure is preferably about 15 to about 160 psia, more preferably from about 30 to about 100 psia. In general, the $H_2:CO$ molar ratio ranges from about 1:10 to 100:1 or higher; the preferred hydrogen to carbon monoxide molar ratio typically being from about 1:1 to about 50:1.

As noted, the hydroformylation process may be conducted at a reaction temperature from about 45° C. to about 200° C. The preferred reaction temperature will of course be dependent upon the operating pressure selected, the identity of the olefinic starting material and catalyst, and the efficiency desired. In general, it is preferred to employ a reaction temperature of from about 60° C. to about 140° C. in most rhodium-catalyzed hydroformylation processes.

In a continuous hydroformylation, and in particular when hydroformylating higher $C_6$ and $C_{30}$ olefinic compounds, the continuous operation involves removing a portion of the liquid hydroformylation reaction medium containing aldehyde product from the hydroformylation reaction zone (hydroformylation reactor); recovering a desired amount of aldehyde product therefrom via vaporization; and recycling the remaining non-volatilized catalyst containing liquid medium back to the hydroformylation reaction zone (e.g. reactor).

During such continuous hydroformylation of higher olefinic compounds using conventional non-polar solvent-soluble and polar solvent-insoluble organophosphorus ligands, aldehyde condensation by-products having a low volatility relative to the organophosphorus ligand of the rhodium hydroformylation catalyst, accumulate at a significant rate and need to be controlled or removed, if one wishes to prolong the effective life span of the cataylst in the continuous hydroformylaton operation, for the reasons mentioned above and such may be accomplished by this invention.

For instance one could maintain the continuous hydroformylation process by treating some or all of the rhodium catalyst containing liquid hydroformylation reaction medium after its removal from the hydroformylation reaction zone (e.g. reactor) either before and/or after, preferably, after, a desired amount of aldehyde product has been recovered via volatilization or distillation from said medium, by the non-polar to polar, back to non-polar extraction treatments of this invention to recover rhodium values thereof removed from such low volatile by-products and returning the non-polar back extracted rhodium-non-polar ligand complex containing organic solution to the hydroformylation reaction medium which remained in the reaction zone (e.g. reactor).

Alternatively the hydroformylation or part of same could be terminated and all of the catalyst-containing non-polar hydroformylation reaction medium so-treated according to this invention to recover the non-polar back extracted rhodium-non-polar ligand complex containing organic solution which can be used either as a source of rhodium for a new hydroformylation reaction medium in the reactor or as a catalytic booster for feeding to any other hydroformylation reaction medium being used in such a hydroformylation process. For example one could shut down one or more hydroformylation reactors of a series of reactors being used, and treat the catalyst containing hydroformylation reaction medium(s) after removing same from the reactor(s) and use the non-polar back extracted rhodium-non-polar ligand complex containing organic solution as disclosed above.

Finally, this invention provides an excellent means for obtaining the rhodium values of a continuous hydroformylation process used for producing $C_7$ and $C_{31}$ aldehydes by employing a conventional non-polar solvent-soluble and polar solvent-insoluble organophosphorus ligand and which process was allowed to continue to build-up the low volatile aldehyde condensation by-products until it is considered no longer feasible to run the process. One need only terminate said process and treat all, or some part if desired, of the rhodium catalyst containing non-polar hydroformylation reaction medium in the same manner as described above and according to this invention to recover the desired rhodium values in their polar extracted rhodium-ionic ligand containing solution from or in their non-polar back extracted rhodium-non-polar ligand containing organic solution form.

Finally, it should be noted and understood, that while the polar extracted rhodium-ionic ligand complex containing organic solution is primarily and preferably employable as a starting material for the non-polar back extraction procedure of this invention such polar extracted rhodium-ionic liquid complex containing polar solution, themselves, may be employed, if desired, as a catalytic booster for other known purposes, such as e.g. in aqueous hydroformylation processes.

FIG. 1 Illustrates a suitable arrangement for treating hydroformylation reaction medium removed from its reactor in order to produce an organic solution containing a reduced level of low volatility components suitable for return to the hydroformylation process.

In accordance with the present invention, hydroformylation reaction medium 13 containing rhodium coordination complex, free organophosphorus ligand and non-polar organic solvent, and also typically containing low volatility aldehyde condensation by-products, is contacted with a polar solution, e.g., an aqueous solution, of an ionic phosphine ligand. In in FIG. 1 embodiment, this contacting is accomplished in an extraction column 40.

For convenience, applicants have identified the form of the rhodium existing in the hydroformylation reaction medium (non-polar organic solution) subsequently exposed to the polar extractant as "a coordination complex" of rhodium and ligand, though it should be understood that the actual complex in the non-polar organic solution may not be exactly the same species as the catalytically active coordination complex formed under hydroformylation reaction conditions. Thus, by characterizing the rhodium complex in this manner, applicants do not intend to imply that the coordination complex of rhodium and ligand which exists, e.g. in a catalyst containing liquid recycle medium, is exactly the same species as the complex present under hydroformation reaction conditions, and the present invention is not so-limited.

If desired, the initial non-polar hydrofomylation reaction medium or initial non-polar organic solution employable as the starting material of this invention can be concentrated, e.g. by vaporization, before the polar extraction of this invention to increase its rhodium concentration. Very high rhodium concentrates also could be prepared e.g. as disclosed in U.S. Pat. No. 4,374,278. Alternatively, additional non-polar organic solvent could be added to the solution in order to lower its density and/or viscosity for facilitating extraction. In any event, the non-polar solution starting material typically will have a rhodium concentration between about 1 to 50,000 ppm and more generally between about 10 to 1,500 ppm, calculated as rhodium metal, and an organophosphorus ligand concentration of up to about 1.5 mols per liter and more usually only up to about 0.5 mol per liter. The catalys solution normally has a ligand to rhodium mol ratio of between about 2 to 200, with a ratio of 50 to 150 being more typical.

It also is possible in some cases to pretreat non-polar organic solution starting materials, when rhodium removal by extraction according to the present invention is less than quantitative, with a chemical reagent to improve or enhance the extraction of rhodium from the non-polar organic solution. Thus, for example, the organic solution can be treated with allyl chloride, allyl acetate, allyl bromide, allyl butyrate, allyl iodide, allyl methacrylate, allyl trifluoroacetate, benzyl acetate, benzyl bromide, diketene, propargyl acetate, propargyl chloride, furfuryl acetate, cyclohexeneoxide, cyclopenteneoxide, propargyl triphenylphosphonium bromide and the like at an elevated temperature of about 60° C. for about 4 hours to increase the rhodium extraction efficiency in such cases.

In the extraction column 40, the substantially non-polar, hydroformylation reaction medium (organic solution) is contacted intimately with a polar solution as defined herein, e.g., an aqueous or methanol solution, 14 containing free polar solvent-soluble ionic organophosphine ligand capable of forming a coordination complex with the rhodium. Generally, once properly modified with ionic moieties to render them polar solvent-soluble, the wide variety of such organophosphine ligands described above in connection with the hydroformylation catalyst solution pontentially can be used. Suitable polar solvent-soluble ionic organophosphine ligands have the general formulae (1) and (2):

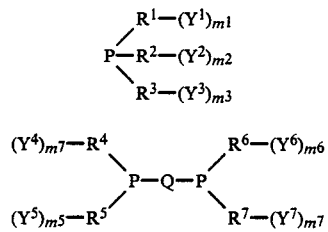

where $R^1$, $R^2$ and $R^3$ of formula (1) and $R^4$, $R^5$, $R^6$ and $R^7$ of formula (2) each individually represent a hydrocarbon radical containing from 1 to 30 carbon atoms selected from the group consisting of alkyl, aryl, alkaryl, aralkyl, and cycloalkyl radicals, where Q in formula (2) represents a divalent organic bridging group and where $Y^1$, $Y^2$ and $Y^3$ of formula (1) and, $Y^4$, $Y^5$, $Y^6$ and $Y^7$ of formula (2) are substituted on the hydrocarbon radical and each individually represents an ionic radical of overall neutral charge selected from the group consisting of;

$SO_3M$ wherein M represents inorganic or organic cationic atoms or radicals selected so that the ligand is polar solvent soluble, e.g. methanol-soluble or water-soluble, $PO_3M$ wherein M represents inorganic or organic cationic atoms or radicals selected so that the ligand is polar solvent soluble, e.g. methanol-soluble or water-soluble, $NR_3X'$ wherein each R represents a hydrocarbon radical containing from 1 to 30 carbon atoms selected from the class consisting of alkyl, aryl, alkaryl, aralkyl, and cycloakyl radicals, and X' represents inorganic or organic anionic atoms or radicals selected so that the ligand is polar solvent soluble, e.g. methanol-soluble or water-soluble, and $CO_2M$ wherein M represents inorganic or organic cationic atoms or radicals selected so that the ligand is polar solvent soluble, e.g. methanol-soluble or water-soluble, wherein $m^1$, $m^2$ and $m^3$ of formula (1) and $m^4$, $m^5$, $m^6$ and $m^7$ of formula (2) are integers which can be the same or different and which can range from 0 to 5. At least one of $m_1$, $m_2$ and $m_3$ and at least one of $m_4$, $m_5$, $m_6$ and $m_7$, cannot be zero (0), i.e., must be equal to or greater than 1, and must have a value sufficient to impart solubility in the polar solvent to the ligand. The integers $m_1$ through $m_7$ indicate the number of ionic radicals of overall neutral charge substituted on each hydrocarbon radical.

The hydrocarbon radicals, $R^1$, $R^2$ and $R^3$ of formula (1) and $R^4$, $R^5$, $R^6$ and $R^7$ of formula (2) preferably contain from 1 to 18 carbon atoms. Hydrocarbon radicals containing from 1 to 12 carbon atoms are more preferred. Such hydrocarbon radicals include those e.g. selected from the group consisting of alkyl, aryl, alkaryl, aralkyl and cycloalkyl. Illustrative hydrocarbon radicals are e.g. methyl, ethyl, propyl, butyl, hexyl, cyclohexyl, phenyl and the like. Most preferably, at least one of $R^1$, $R^2$ and $R^3$ in formula (1) and at least one of $R^4$, $R^5$, $R^6$ and $R^7$ in formula (2) is a phenyl radical. Such hydrocarbon radicals may contain one or more substituents provided that they do not unduly adversely affect the use of the ligand and this invention. Suitable substituents, in addition to the necessary ionic substituent, e.g, the sulfonate, carboxylate and the like, include straight and branched chain alkyl groups, preferably of 1 to 4 carbon atoms, alkoxy groups, halogen atoms, hydroxy, cyano, nitro and amino groups and the like. More preferably at least two, and most preferably three of $R^1$, $R^2$ and $R^3$ in formula (1) are phenyl groups and at least three and most preferably four of $R^4$, $R^5$, $R^6$ and $R^7$ in formula (2) are phenyl radicals.

The organic divalent bridging group represented by Q in the above formulas is a divalent radical containing from 1 to 30 carbon atoms selected from the group consisting of hydrocarbon radicals, oxygen containing hydrocarbon radicals (i.e. hydrocarbon radicals interrupted with an oxygen atom), sulfur containing hydrocarbon radicals (i.e. hydrocarbon radicals interrupted with sulfur atom) and nitrogen containing hydrocarbon atoms (i.e. hydrocarbon radicals interrupted with a nitrogen atom). Preferably such radicals contain from 1 to 16 and more preferably from 1 to 12 carbon atoms. Illustrative divalent hydrocarbon radicals include alkylene radicals (e.g. methylene (—CH$_2$—), ethylene, propylene, isopropylene, butylene, 1,2-dimethylethylene, t-butylene, neopentylene, 2-methypropylene, hexylene, 2-ethylhexylene, dodecylene, eicosylene, and the like); arylene radicals (e.g. phenylene, substituted phenylene, diphenylene, substituted diphenylene, and the like); as well as alkylene containing arylene radicals (e.g. methylenephenylene (—CH$_2$C$_6$H$_4$—), ethylenephenylethylene (—C$_2$H$_4$C$_6$H$_4$—C$_2$H$_4$—), phenylenepropylphenylene (—C$_6$H$_4$C(CH$_3$)$_2$C$_6$H$_4$—), methylenediphenylmethylene (—CH$_2$C$_6$H$_4$C$_6$H$_4$CH$_2$—), and the like); alkylidene radicals (e.g. ethylidene (—CH=CH—), and the like); and the like. Illustrative oxygen containing hydrocarbon radicals include alkyleneoxyalkylene radicals (e.g. ethyleneoxymethylene (—C$_2$H$_4$OCH$_2$—), propyleneoxymethylene (—C$_3$H$_6$OCH$_2$—), ethyleneoxyethylene (—C$_2$H$_4$OC$_2$H$_4$—), 1,2-bis(ethyleneoxy)ethane (—C$_2$H$_4$OC$_2$H$_4$OC$_2$H$_4$—), propyleneoxypropylene (—C$_3$H$_6$OC$_3$H$_6$—) and the like); aryleneoxyalkylene radicals (e.g. phenyleneoxymethylene (—C$_6$H$_4$OCH$_2$—), and the like); and the like. Illustrative sulfur or thio containing hydrocarbon radicals include alkylenethioalkylene radicals (e.g. ethylenethioethylene (—C$_2$H$_4$SC$_2$H$_4$—), 1,2-bis(ethylenethio)ethane (—C$_2$H$_4$SC$_2$H$_4$SC$_2$H$_4$—), propylenethiomethylene (—C$_3$H$_6$SCH$_2$—), propylenethiopropylene (—C$_3$H$_6$SC$_3$H$_6$—), and the like); arylenethioalkylene radicals (e.g. phenylenethiomethylene (—C$_3$H$_6$S—CH$_2$—), and the like); and the like. Illustrative amino containing hydrocarbon radicals include alkyleneaminoalkylene radicals (e.g., methyleneaminomethylethylene (—CH$_2$N(CH$_3$)C$_2$H$_4$—), ethyleneaminomethylethylene (—C$_2$H$_4$N(CH$_3$)C$_{2\neq H4}$), bis(ethyleneaminomethyl)ethane (—C$_2$H$_4$N(CH$_3$)C$_2$H$_4$N(CH$_3$)C$_2$H$_4$—), propyleneamino methylpropylene (—C$_3$H$_6$N(CH$_3$)C$_3$H$_6$—) and the like; and the like. Most preferably Q is a divalent hydrocarbon radical, especially a divalent alkylene radical containing from 2 to 8 carbon atoms.

Particularly, suitable ionic organophosphine ligands are the ionic triarylphosphines and, in particular, the salts of sulfonated and of carboxylated triarylphosphines, as, for example, are described in U.S. Pat. Nos. 4,248,802; 4,399,312; 4,668,824; 4,716,250 and 4,731,486; and European Patent Application, Pub. No. 216,315 (published Apr., 1987). Preferred among this group are the salts of monosulfonated and of trisulfonated triphenylphosphines, and the salts of monocarboxylated and of tricarboxylated triphenylphosphine. Another suitable class of ionic organophosphines are ionic bis-diarylphosphines such as bisdiphenylphosphinoethane monosulfonate salts. Mixtures of suitable ionic phosphine ligands also can be employed.

Such polar solvent-soluble, ionic organophosphine ligands capable of forming a coordination complex with rhodium embraced by the above formulae, as well as methods for their preparation, are well-known in the art and need not be described in detail. See for example J. Chem. Soc. (1958), pp. 276–288 and U.S. Pat. Nos. 4,248,802; 4,399,312; 4,483,802; 4,633,021; 4,668,824; 4,716,250 and 4,731,486, all incorporated herein by reference. For example sulfonated ligands may be prepared by sulfonating the corresponding phosphine, e.g. triphenylphosphine, with fuming sulfuric acid (oleum) under controlled temperature conditions.

The ionic phosphine ligands are used in the present invention in their polar solvent-soluble, e.g. water-soluble or methanol-soluble, salt form. As suitable counterions, M, for the anionic moieties of the ionic phosphine salts there can be mentioned the cations of the alkali and alkaline earth metals, e.g., lithium, sodium, potassium, cesium, rubidium, calcium, barium, magnesium and strontium, the ammonium cation and quaternary ammonium cations. Suitable anionic atoms or radicals include, for example, sulfate, carbonate, phosphate, chloride, acetate, oxalate and the like. Of course, it is understood that the number of anionic and cationic moieties in a ligand molecule also depends on the valences of the ions (ionic radical) and counter-ions (M and X') of any particular ligand.

The polar phase should contain an amount of the polar solvent-soluble, ionic organophosphine ligand sufficient to extract rhodium from a non-polar organic solution containing non-polar organic solvent-soluble and polar solvent-insoluble rhodium-organophosphorus ligand coordination complex. If the solubility of the coordination complex formed as a result of the contacting is greater in the non-polar organic phase than in the polar phase, e.g. than in water or in methanol, then the particular polar solvent-soluble ionic organophosphine used is not well-suited for the extraction. The required amount of polar solvent-soluble ligand in any particular circumstance will be influenced, inter alia, by the nature and amount of the non-polar organic solvent-soluble ligand in the non-polar organic solution, by the concentration of rhodium in the non-polar organic solution, by the particular polar solvent-soluble, ionic ligand in the polar phase, and by the extraction conditions. Generally, routine experimentation can be used to determine the suitability of any particular ionic ligand as an extractant as well as to determine both a suitable concentration of the ionic ligand for the polar extractant and suitable extraction conditions. Typically, the polar solution will contain a concentration of at least about 0.03 mol per liter of the polar solvent-soluble ionic organophosphine ligand and preferably at least about 0.1 mol per liter.

While the necessary level of polar solvent-soluble ionic ligand in the polar solution to the amount of non-polar solvent-soluble ligand in the non-polar organic solution satisfactory for accomplishing the desired extraction is influenced as noted above, by the particular ligands employed, routine experimentation can be used to identify an optimum ratio. Normally, to ensure a satisfactory extraction of rhodium from the non-polar solution there should be sufficient polar solvent-soluble, ionic organophosphine ligand in the polar phase to yield a ratio of the molar concentration of non-polar organic solvent-soluble and polar solvent-insoluble ligand (non-polar ligand) in the non-polar phase to the molar concentration of polar solvent-soluble ligand (polar ligand) in the polar phase of below about 20, more generally below about 10 and most generally below about 5. For economic reasons, the highest molar concentration ratio of non-polar ligand to polar ligand that yields the desired extraction should be employed.

The upper limit of the polar solvent-soluble ligand concentration is not critical and in part is determined by the solubility of the ionic ligand in the polar solvent. However, since ultimate recovery of the rhodium likely will be accompanied by some loss of polar solvent-soluble ionic ligand, too large an excess of polar solvent-soluble ligand preferably is to be avoided. Generally, based on economic considerations, a polar solvent-soluble ionic ligand concentration below about 0.3 mol per liter, and, more usually below about 0.2 mol per liter, should be suitable in most circumstances.

The polar solution also may include other adjivants to facilitate the transfer (extraction) of rhodium into the polar phase. For example a neutral salt, e.g., sodium sulfate or phosphate, could be added to the polar phase to increase its density and thus facilitate its phase separation from the non-polar solvent organic phase.

Depending inter alia on the nature of the polar solvent-soluble ligand employed and the use or non-use of any of chemical pretreatment, the polar solution may extract only catalytically active forms of the transition metal, e.g. to the active forms to rhodium, from the hydroformylation reaction medium or organic solution, or may extract both catalytically active and catalytically inactive forms of the transition metal, e.g. rhodium. Thus, the language used through the specification and claims describing the extraction of transition metal is contemplated to include the extraction of only catalytically active forms of the transition metal, as well as the concurrent extraction of both catalytically active and catalytically inactive forms of the transition metal. Applicants have found that the ionic monophosphines tend to extract only the active form of rhodium. Obviously, the particular polar solvent-soluble, e.g. water-soluble, ionic organophosphine ligand chosen can be tailored to obtain any variety of desired results.

While the non-polar organic solution and polar solution preferably are flowed countercurrent to one another in an extraction column, any other known extraction techniques also could be employed and any modfications thereof needed to obtain a desired degree of rhodium removal from the non-polar phase will be apparent to those skilled in the art. Thus, the polar extraction step can be accomplished using a wide variety of known techniques and conventional equipment. Preferably, the polar extraction is carried out in a continuous manner using either continuous countercurrent multi-stage contacting procedures employing a series of mixer-settlers or a trayed column or by countercurrent differential contact in a packed tower, rotary-disc contacting column and the like. Equipment suitable for accomplishing the polar extraction will be apparent to those skilled in the art and need not be described in any detail.

A volume ratio of the non-polar organic solution (O) to the polar solution (A) introduced into the extractor, e.g. the extraction column, of from about 0.01 to 100 generally should be satisfactory for transferring rhodium into the polar phase, contacting (volume) ratios (O/A) between about 1 to 10 are more typical. An optimum value for any specific set of circumstances can be determined using routine experimentation.

The temperature for the contacting (polar extraction) also is not critical and to a certain extent depends upon the specific compositions of the non-polar organic solution and the polar solution. Generally, under atmospheric pressure operation, a temperature of from about ambient up to about 100° C. is satisfactory with a temperature between about ambient (e.g. 25° C.) and 60° C. being preferred. In any event, any condition of temperature and pressure at which the non-polar organic solution and the polar solution remain immiscible and in the liquid state can be employed.

The contacting time also is not critical and need only be sufficient to accomplish the desired extraction of the rhodium from the non-polar phase. A contact time between about 1 minute and 24 hours should prove adequate in most instances. A contact time betwen about 3 and 30 minutes is more typical. An appropriate contacting period can be determined using routine experimentation. This contacting of the polar solution and the non-polar organic solution causes rhodium to transfer from the non-polar organic solution e.g. hydroformylation reaction medium into the polar solution.

Organic solution recovered from the overhead of the extraction column in line 15 contains residual rhodium, non-polar organic solvent-soluble organophosphorus ligand and non-polar organic solvent, e.g., aldehyde product and higher boiling liquid aldehyde condensation by-products in the case of hydroformylation. If desired, this stream can be treated separately to recover both residual organophosphorus ligand and any residual rhodium. The polar solution recovered from the bottom of the extraction column in line 16 will contain rhodium that was present in the original non-polar organic solution starting material. By appropriately treating this polar solution, it is possible to transfer the rhodium back into a non-polar organic solvent, which in the specific case of hydroformylation should be suitable for reuse in a hydroformylation reaction medium as catalyst.

In accordance with a preferred aspect of the present invention, the polar solution in line 16 is treated in treatment zone 50 with a conditioning reagent, introduced through line 17, in order to reduce the amount, in the polar solution, of the polar solvent-soluble ionic organophosphine ligand capable of complexing with the rhodium. In other words, the polar solution is treated so that the complex-forming ability of polar solvent-soluble ligand is rendered incapable or less capable of forming a coordination complex with rhodium. If desired, the concentration of rhodium in the polar solution can be concentrated, e.g. by vaporization, before or after treatment with the conditioning reagent. In any event, a polar solution generally will be obtained having a rhodium concentration of from about 1 to 50,000 ppm, and more typically between about 500 and 2,500 ppm, calculated as rhodium metal.

In accordance with the present invention, the polar solution can be treated with a variety of conditioning reagents in order to reduce the amount of (i.e. chemically degrade or alter) the polar solvent-soluble ionic organophosphine ligand. For example, the polar solution can be treated with an ylid precursor such as maleic acid, with a strong acid such as sulfuric acid, with an alkylating agent such as methyl iodide or with a oxidizing reagent such as hydrogen peroxide or an organic peroxide. The conditioning reagent should react with the polar solvent-soluble ligand to produce products that lack a coordinating affinity for the rhodium. Preferably, the reaction products are polar-soluble and non-polar organic solvent-insoluble so that they are not back-extracted into the non-polar organic solvent during subsequent treatment. Treatment with the conditioning reagent thus reduces the amount, in the polar solution, of polar solvent-soluble ligand capable of strongly coordinating with rhodium.

Although not particularly critical, the polar solution preferably is treated with the conditioning reagent at a temperature of between about 0° to 250° C. for a time between about 0.1 to 24 hours. In any event, the solution should be treated under conditions necessary to reduce the amount of ligand capable of complexing with the rhodium by an amount sufficient to permit back-extraction of rhodium into a non-polar organic solvent which contains a non-polar organic solvent-soluble and polar solvent-insoluble organophosphorus ligand. A treatment temperature of about 25° to 60° C. for a time period of one to four hours should be adequate in most cases.

While the degree of reduction in the amount of the polar solvent-soluble ligand in any particular circumstance will be influenced, inter alia, by the nature and initial concentration of the polar solvent-soluble ligand itself, by the nature and amount of the non-polar organic solvent-soluble and polar solvent-insoluble ligand in the organic back-extractant and by the conditions of the back extraction, it is preferred to reduce the amount of polar solvent-soluble ligand by at least about 70% and preferably by at least about 85%. An amount of residual polar solvent-soluble ligand of below about 10 equivalents, i.e., 10 mols of ligand per gram atom of rhodium, and preferably below about 5 equivalents is especially preferred. Best results are obtained if the rhodium coordination ability of the polar solvent-soluble ligand is completely destroyed.

Suitable ylid precursors for use in the present invention as conditioning reagents are unsaturated compounds containing from 2 to 18 carbon atoms, preferably from 3 to 10 carbon atoms, and can be selected from the group consisting of unsaturated compounds having

  (A)

wherein X is a radical selected from the group consisting of

—CN, —Cl, —Br, —I, —NO$_2$, and —OR$^{12}$; R$^{11}$ is a radical selected from the group consisting of hydrogen, alkyl, aryl, hydroxy, alkoxy, amino and halogen; R$^{12}$ is an alkyl or aryl radical; and R$^8$, R$^9$ and R$^{10}$ individually are radicals selected from the group consisting of hydrogen, alkyl, aryl, X radicals as defined above —CH$_2$X radicals wherein X is the same as defined above; and wherein R$^8$ and R$^9$ taken together can form an alkylene group having from 2 to 8 carbon atoms; and anhydrides of the carboxylic acids of the unsaturated compounds within the scope of formula (A). Maleic acid and maleic anhydride are particularly useful reagents.

A strong acid conditioning reagent suitable for treating the polar solution may be an inorganic or organic acid. Such inorganic acids as hydrochloric, sulfuric, nitric, phosphoric and such organic acids such as methanesulfonic acid and para-toluenesulfonic acid are suitable. Many others will be apparent to those skilled in the art. Sulfuric acid is preferred. To an extent, treatment with a strong acid conditioning agent is reversible. Thus the complex-forming ability of polar solvent-soluble ligand previously rendered incapable of forming a coordination complex with rhodium by treatment with the strong acid, can, by subsequent treatment with an appropriate alkaline reagent, such as sodium hydroxide, be restored.

Acceptable alkylating reagents for use as the conditioning reagent can be selected from the class of compounds capable of reacting with the polar solvent-soluble ionic organophosphine ligand to form a polar solvent-soluble phosphonium salt thereof. Compounds of this class are monovalent hydrocarbon halides, such as methyl iodide (see U.S. Pat. No. 4,429,161, the disclosure of which is incorporated herein by reference).

An oxidizing agent suitably employed in this invention as the conditioning reagent may be supplied in the form of a gas of liquid and can be selected from oxygen, hydrogen peroxide, and organic peroxides, metal oxidizing reagents and peracids which preferably form polar solvent-soluble oxidation by-products with the polar solvent-soluble organophosphine ligand. Hydrogen peroxide is a particularly suitable oxidizing agent. It is to be understood that oxygen need not be employed in its pure form, but more preferably and conveniently is employed in the form of air or in admixture with an inert gas, such as nitrogen in order to minimize any explosive hazards.

The liquid organic peroxides, which may also be employed as oxidants herein, preferably encompass polar solvent-soluble organic peroxides of the formula R—O—O—R′, wherein R represents a radical selected from the group consisting of monovalent hydrocarbon radicals of 2 to 20 carbon atoms, carboxylic acyl radicals of 2 to 20 carbon atoms, aroyl radicals of 7 to 20 carbon atoms and cycloalkoxycarbonyl radicals of 4 to 20 carbon atoms, and wherein R′ represents a radical selected from the group consisting of hydrogen and a radical represented by R as defined above. Preferred monovalent hydrocarbon radicals represented by R and R′ above are alkyl and aralkyl radicals, especially t-alkyl radicals of 4 to 20 carbon atoms and aralkyl radicals of 8 to 15 carbon atoms. Most preferably R′ represents hydrogen (i.e., —H). Illustrative organic peroxides include t-butyl hydroperoxide, t-amyl hydroperoxide, cumene hydroperoxide, ethylbenzene hydroperoxide, and the like. Such organic peroxides and/or methods for their preparations are well known in the art.

The polar solution recovered from this treatment in line 18 of FIG. 1, having a lowered amount of rhodium complex-forming, polar solvent-soluble ionic organophosphine ligand then can be contacted (back-extracted) with an immiscible, non-polar, organic solvent containing a non-polar organic solvent-soluble and polar solvent-insoluble organophosphorus ligand. The back extractant is introduced into extraction means or zone 60 through line 19. The same non-polar organic solvent-soluble and polar solvent-insoluble ligands previously described as being useful for hydroformylation can be employed. As with the first extraction, the contacting typically can be done in an extraction column 60. Again, any substantially non-polar organic solvent which forms a separate, distinct phase in the presence of a polar phase, e.g., an aqueous phase, and, in the specific case of hydroformylation, which does not adversely affect (i.e., which is preferably compatible with) the desired hydroformylation reaction medium can be employed. Particularly useful non-polar solvents are those known to be suitable for use in prior art hydroformylation processes as described previously herein. The non-polar organic solution used for back extraction preferably contains the same non-polar organic solvent-soluble and polar solvent-insoluble organophosphorus ligand which is to be used in the hydroformylation reaction medium.

The non-polar organic solvent should contain an amount of the non-polar organic solvent-soluble and polar solvent-insoluble organophosphorus ligand sufficient to back-extract rhodium from the treated polar solution. The necessary concentration of the non-polar organic solvent-soluble and polar solvent-insoluble ligand will depend, inter alia, on the nature and residual level of the polar-soluble ionic phosphine ligand in the polar solution (e.g., aqueous phase), on the particular non-polar organic solvent-soluble and polar solvent-insoluble ligand and its amount in the organic solvent and on the extraction conditions. Generally, routine experimentation can be used to determine the suitability of any particular non-polar solvent-soluble ligand as a back extractant, as well as to determine both a suitable ligand concentration for the non-polar solvent and suitable extraction conditions. Typically, the non-polar organic solvent will contain about 0.01 to 1.0 mols per liter of the non-polar organic solvent-soluble and polar solvent-insoluble organophosphorus ligand and normally will contain about 0.03 to 0.6 mols per liter. Normally to ensure a satisfactory extraction of rhodium from the polar solution, there should be sufficient non-polar organic solvent-soluble and polar solvent-insoluble ligand in the organic solvent to yield a ratio of the molar concentration of non-polar organic solvent-soluble and polar solvent-insoluble ligand in the organic solvent (non-polar ligand) to the molar concentration of residual polar solvent-soluble ionic ligand capable of forming a coordination complex with rhodium in the polar phase (polar ligand) of above about 10, preferably above about 20, and most preferably above about 30. Conditions and equipment for the back-extraction step can be the same as those employed in the initial organic-polar contacting step used to transfer rhodium from the catalyst solution to the polar solution.

In the case of hydroformylation, an organic solution of ligand-rhodium complex suitable for use in a hydroformylation reaction medium is recovered as overhead from extraction column 60 in line 22, while a polar solution, e.g., an aqueous solution, with a reduced concentration of rhodium is recovered from the column's bottom in line 21. This polar solution can be used to prepare polar solvent-soluble ionic organophosphine ligand-containing polar solution used for again contacting hydroformylation reaction medium. The organic solvent containing the extracted rhodium can be used for any number of purposes as described above.

In the case where hydroformylation reaction medium is treated in accordance with the present invention, applicants have found that the rhodium transferred back into the ligand-containing organic solvent, using either of the alternative embodiments described above, becomes substantially active under hydroformylation reaction conditions when subsequently used for hydroformylation catalysis.

The following examples are illustrative of the present invention and are not to be regarded as limiting. It should be understood that all of the parts, percentages, and proportions referred to herein and in the appended claims are by weight unless otherwise indicated. In the following examples, the ionic phosphine ligand, 3-(diphenylphosphino)-benzenesulfonic acid, sodium salt is referred to in the alternative as the sodium salt of triphenylphosphine monosulfonic acid and as TPPMS-Na, the ionic phosphine ligand tri(sulfopheny)phosphine, sodium salt is referred to in the alternative as the sodium salt of triphenylphosphine trisulfonic acid and as TPPTS-Na; finally the ionic phosphine ligand bisdiphenylphosphinoethane m-monosulfonic acid, sodium salt, is referred to in the alternative as the sodium salt of DIPHOS-monosulfonic acid and as S-DIPHOS-Na.

The activities of the hydroformylation catalysts, as reported in the following examples, were determined, and other solutions were activated, using a small batch, low pressure-oxo hydroformylation reactor operated at a temperature of about 100° C. and at a pressure of about 90–95 psia with a feed mixture of an equimolar amount of propylene, carbon monoxide and hydrogen. In all the batch extraction examples, the contacting of the non-polar organic phase and polar phase was done in standard laboratory glassware at about 50° to 60° C. for about 15 to 30 minutes. The phases were allowed to separate and each was recovered. In some cases the organic phase was contacted with fresh polar phase one or two additional times, as noted, to simulate multi-stage extraction. In such cases of multiple contacting, the rhodium recovery is determined by summing the rhodium removed by each extraction.

Rhodium concentrations were determined using atomic absorption spectroscopy (AAS), non-polar organic solvent-soluble ligand concentrations were determined using vapor phase chromotography (VPC), while the ionic phosphine ligand concentrations were determined using high performance liquid chromotography (HPLC). Such procedures are well-known to those skilled in the art.

EXAMPLES 1–4

In these examples, the ability of polar solutions, i.e., aqueous solutions, containing different concentrations of a polar solvent-soluble ionic phosphine ligand to extract active rhodium from a fresh (100% active), non-polar hydroformylation reaction medium containing 10% by weight triphenylphosphine (TTP) ligand and 300 ppm rhodium in Texanol ® solvent (Eastman brand 2,2,4-trimethyl-1,3-pentanediol monoisobutyrate) was examined. The sodium salt of triphenylphosphine monosulfonic acid (TPPMS-Na) was used as the polar solvent-soluble, i.e., water-soluble, ionic phosphine ligand. In each example, a fifty gram sample of the reaction medium (a 49.25 gm sample was used in Example 4), was contacted (extracted) with three separate 10 gm samples of aqueous ligand solution (only two separate 10 gm samples were used for Example 4). The results are presented in Table 1 and illustrate the rhodium recovery as a function of water-soluble ligand concentration.

TABLE 1

| Example No. | TPPMS-Na Conc. (%) | Rhodium Recovery (%) |
|---|---|---|
| 1 | 1.0 | 84 |
| 2 | 3.0 | 97 |
| 3 | 5.0 | 99 |
| 4 | 10.0 | 99 |

EXAMPLES 4 and 5

In these examples, the extraction abilities of a 10% by weight polar solution of the sodium salt of triphenylphosphine monosulfonic acid (TPPMS-Na) (Example 4) and a 10% by weight polar solution of the sodium salt of triphenylphosphine trisulfonic acid (TPPTS-Na) (Example 5) were examined. In both cases the non-polar hydroformylation reaction medium contained 10% by weight triphenylphosphine ligand (TPP) and 300 ppm rhodium in Texanol ® and had an activity of 100%. In each case, two equally sized, sequential aqueous washes (extractions) were used. However, since the sample size of the organic phase was smaller in Example 5, its organic/aqueous (O/A) volume ratio was smaller. Table 2 presents the results obtained.

TABLE 2

| Example No. | Aqueous Ligand | Organic/Aqueous Vol. ratio | Rhodium Recovery (%) |
|---|---|---|---|
| 4 | TPPMS-Na | 2.8 | 99 |
| 5 | TPPTS-Na | 1.1 | 86.3 |

EXAMPLES 6 and 7

In these examples a 3% by weight aqueous (polar) solution of the sodium salt of triphenylphosphine monosulfonic acid (Example 6) and a 10% by weight aqueous (polar) solution of the sodium salt of triphenylphosphine trisulfonic acid (Example 7) were used to extract active rhodium from spent hydroformylation reaction medium having an activity of 75%, a rhodium concentration of 727 ppm, a triphenylphosphine (TPP) ligand concentration of 10% by weight, 80% by weight pentadecanal and the balance hydroformylation aldehyde condensation by-products. In each case, two sequential, equally sized aqueous washes (extractions) were used. However, since the sample size of the organic phase was smaller in Example 7, its organic/aqueous (O/A) volume ratio was smaller. Table 3 presents the results obtained.

TABLE 3

| Example No. | Aqueous Ligand | Organic/Aqueous Vol. ratio | Aqueous Ligand Conc. | Rodium Recovery (%) |
|---|---|---|---|---|
| 6 | TPPMS-Na | 2.8 | 3.0 | 74.5 |
| 7 | TPPTS-Na | 1.1 | 10.0 | 74.7 |

EXAMPLES 8 and 9

These examples report the abilities of a 10% by weight aqueous (polar) solution of TPPMS-Na (Example 8) and a 10% by weight aqueous (polar) solution of TPPTS-Na (Example 9) to extract active rhodium from a spent hydroformylation reaction medium having an activity of 39%, a rhodium concentration of 540 ppm, 10% by weight triphenylphosphine (TPP) ligand, 30% by weight butyraldehyde and the balance aldehyde condensation by-products. In each case, two equally sized aqueous washes (extractions) were used. Example 9 used a slightly smaller sized catalyst solution sample. The results are presented in Table 4.

TABLE 4

| Example No. | Aqueous Ligand | Organic/Aqueous Vol. ratio | Rhodium Recovery (%) |
|---|---|---|---|
| 8 | TPPMS-Na | 1.2 | 38.0 |
| 9 | TPPTS-Na | 1.1 | 38.9 |

EXAMPLES 10 and 11

These examples report the abilities of 10% by weight aqueous (polar) solutions of TPPMS-Na (Example 10) and TPPTS-Na (Example 11) to extract active rhodium from a reactivated hydroformylation reaction medium prepared in accordance with U.S. Pat. No. 4,297,239 having an activity of 70%, a rhodium concentration of 8,100 ppm, 1.0% by weight free triphenylphosphine (TPP) ligand and the remainder consisting essentially of high boiling aldehyde condensation by-products and triphenylphosphine oxides. In each case a 25 gram sample of the organic phase was sequentially twice extracted with the aqueous phase. Two 35 gram aqueous washes were used for Example 11, while more aqueous extractant (two 55 gram samples) was used in Example 11 to yield the lower O/A value. The results are presented in Table 5.

TABLE 5

| Example No. | Aqueous Ligand | Organic/Aqueous Vol. ratio | Rhodium Recovery (%) |
|---|---|---|---|
| 10 | TPPMS-Na | 0.38 | 52.7 |
| 11 | TPPTS-Na | 0.24 | 33.9 |

EXAMPLE 12

A 25 gram sample of a hydroformylation reaction medium of unknown activity containing 200 ppm of rhodium, 1.5% by weight of 2-t-butyl-4-methoxy [3,3'-di-t-butyl-5,5'-dimethoxy-1,1'-biphenyl-2,2'-diyl] phosphite ligand and the remainder consisting essentially of valeraldehyde and its condensation by-products was sequentially extracted twice with 25 gram samples of an aqueous (polar) solution containing 5.0% by weight TPPMS-Na; 94% of the rhodium was recovered in the two aqueous wash fractions.

EXAMPLE 13

A 10 gram sample of fresh hydroformylation catalyst solution (100% activity) containing 1000 ppm of rhodium, 20% by weight triphenylphosphine (TPP) ligand, 24% by weight butyraldehyde and the balance Texanol ® was contacted once with 5.9 grams of a 3.0% by weight aqueous (polar) solution of TPPMS-Na. 69.7% of the rhodium was recovered in the aqueous phase.

EXAMPLE 14–17

These examples illustrate the use of maleic acid (MA) as a conditioning reagent for reducing the amount in a polar solution, e.g., in an aqueous solution, of the polar solvent-soluble organophosphine ligand capable of forming a coordination complex, i.e. capable of complexing, with rhodium and the effect on the polar to non-polar extraction efficiency. The aqueous solution was obtained by extracting a non-polar hydroformylation catalyst solution containing 540 ppm rhodium, 10% by weight TPP, 30% by weight butyraldehyde and the balance aldehyde condensation by products with an aqueous solution containing 5% by weight TPPMS-Na. Twenty gram samples of the resultant aqueous solution containing 5% by weight TPPMS-Na and 489 ppm rhodium were treated by mixing with various amounts of maleic acid at a temperature of 50° C. for 30 minutes to convert water-soluble ionic ligand in each sample to a water-soluble non-coordinating form. The maleic acid-treated samples then were back extracted using a Texanol ® solution containing 10% by weight triphenylphosphine (TPP). Each treated sample was washed three times with 20 gram portions of the Texanol ® ligand solution. The results are presented in Table 6. As shown, by reducing the ligand concentration in the aqueous phase to less than 5.0 mols of ligand per gram-atom of rhodium (which in these cases also corresponded to greater than about 85% ligand removal), excellent back-extraction of the rhodium was realized.

TABLE 6

| Example No. | Reduction in Aqueous Ligand Conc. (%) | TPPMS-Na/ Rhodium mol ratio | Rhodium Recovered (%) |
|---|---|---|---|
| 14 | 86.8 | 3.8 | 98.8 |
| 15 | 84.6 | 4.4 | 97.3 |
| 16 | 70.4 | 8.6 | 48.3 |
| 17 | 50.2 | 14.4 | 3.7 |

EXAMPLES 18-21

These examples illustrate the use of different levels of maleic acid (MA) as a conditioning reagent for reducing the amount of TPPMS-Na ligand capable of complexing with rhodium in aqueous (polar) solutions containing various amounts of rhodium and the effect of such treatment on rhodium extraction efficiency. The aqueous solution used in Examples 18 and 20 correspond to the aqueous solutions obtained in Examples 6 and 8 respectively; while the aqueous solutions for Examples 19 and 21 were obtained by extracting nonpolar hydroformylation catalyst solutions containing 300 ppm rhodium, 10% by weight TPP and the balance Texanol®, and 375 ppm rhodium, 11% by weight TPP, 6% by weight butyraldelhyde and the balance aldehyde condensation by-products respectively with 10% by weight aqueous solution of TPPMS-Na and a 5% by weight aqueous solution of TPPMS-Na. The MA-treated aqueous (polar) solutions were each back-extracted three times using 25 gm portions of a 10% by weight solution of triphenylphosphine in Texanol®. The aqueous solutions containing the added maleic acid were heated at 50° C. for about 30 minutes. The results are presented in Table 7, and demonstrate the effectiveness of maleic acid in conditioning the aqueous solution for extraction.

TABLE 7

| Example No. | Aqueous Rh Conc (PPM) | TPPMS-Na/MA mass ratio | Organic/ Aqueous Vol. ratio | Rodium Recovery (%) |
|---|---|---|---|---|
| 18 | 260 | 3.3 | 0.83 | 100 |
| 19 | 650 | 3.4 | 4.9 | 90.6 |
| 20 | 412 | 2.4 | 4.9 | 97.6 |
| 21 | 342 | 2.9 | 1.2 | 98.0 |

EXAMPLE 22

This Example illustrates the use of an organic solution of cyclohexyldiphenylphosphine (CHDPP) ligand for extracting rhodium from an aqueous extractant solution. A 25 gram sample of an aqueous solution containing 5% by weight TPPMS-Na, used to extract rhodium from spent hydroformylation reaction medium containing 540 ppm rhodium, 10% by weight TPP, 30% by weight butyraldehyde and the balance aldehyde condensation by-products, contained 78 ppm rhodium after such extraction. The sample was treated at 50° C. for about 30 minutes with 0.4 grams of maleic acid and then was extracted three times (25 gram portions) using a 3.0% by weight solution of CHDPP in Texanol® solvent. Analysis of the cumulative organic extractants showed that 96.9% of the rhodium was transferred from the aqueous solution into the organic phase.

EXAMPLE 23-26

These examples illustrate the use of strong acid conditioning reagents for converting TPPMS-Na ligand in aqueous (polar) solutions containing various amounts of rhodium to a non-coordinating form, i.e. less capable of complexing with rhodium, and the effect of such treatment on extraction efficiency. In Example 23, the original aqueous solution was obtained by extracting a non-polar hydroformylation catalyst solution containing 540 ppm rhodium, 10% by weight TPP, 30% by weight butyraldehyde and the balance aldehyde condensation by-products with an aqueous solution of 5% by weight TPPMS-Na; in Examples 24 and 25 the original aqueous solutions were obtained by extracting a non-polar hydroformylation catalyst solution containing 1000 ppm rhodium, 20% by weight TPP, 24% by weight butyraldehyde and the balance Texanol® with aqueous solutions of 3% by weight TPPMS-Na, and in Example 26, the original aqueous solution was obtained by extracting a non-polar hydroformylation catalyst solution containing 300 ppm rhodium, 3% by weight TPP and the balance Texanol® with an aqueous solution of 5% by weight TPPMS-Na. The acid-treated aqueous solutions were each sequentially extracted three times (25 gm portions) using a 10% by weight solution of triphenylphosphine (TPP) in Texanol® solvent. The aqueous solutions containing the added acid were heated at 50° C. for about 30 minutes. The results are presented in Table 8 and demonstrate the effectiveness of strong acid treatment for conditioning the aqueous (polar) solution for extraction of rhodium from the aqueous phase.

TABLE 8

| Example No. | Aqueous Rh Conc. (ppm) | Strong Acid Reagent | TPPMS-Na/Acid Mass ratio | Organic/Aqueous Vol. Ratio | Rhodium Recovery (%) |
|---|---|---|---|---|---|
| 23 | 281 | HCl | 2.8 | 2.9 | 96.1 |
| 24 | 933 | $H_2SO_4$ | 3.3 | 4.2 | 97.3 |
| 25 | 906 | $H_2SO_4$ | 1.7 | 4.2 | 99.6 |
| 26 | 200 | $H_2SO_4$ | 0.4 | 10.4 | 97.0 |

EXAMPLE 27

This example describes the continuous extraction of rhodium from hydroformylation reaction medium using a 3/8 inch diameter extraction column having five (5) theoretical stages and counter current flow of the organic solution and an aqueous solution containing TPPMS-Na ligand. The combined feed rate to the extraction column (organic phase plus aqueous phase) was maintained at about 1700 gm/hour in all the runs and the column was operated at about 35° C. A rhodium balance was determined for each run from the feed rates and rhodium concentrations of the various streams and is reported in Tables 9 and 10. Extraction efficiencies were calculated by determining the percentage of rhodium transferred from the organic phase to the aqueous phase and then normalizing the value by dividing it with the catalyst activity. The results are presented in Tables 9 and 10.

Table 9 illustrates the effect of reducing the amount of the aqueous feed relative to the organic feed. In these runs a 5.0% by weight polar solution of TPPMS-Na was used to extract rhodium from an organic solution having a 39% activity as a hydroformylation catalyst and containing 1073 ppm rhodium, 15% by weight TPP, 38% by weight butyraldehyde, 10% by weight hexane, 10% by weight C$_9$ aldehyde and the balance butyraldehyde condensation by-products. This same hydroformylation catalyst solution also was used for run number 8 in Table 10. The results show that as the amount of aqueous feed is reduced (i.e. as the organic-/aqueous (O/A) volume ratio increases) the extraction efficiency decreased. Due in part to the viscous nature of the organic solution, larger O/A ratios do not permit sufficient exposure of the rhodium in the organic phase to the aqueous extractant phase. Table 10 presents the remaining data. Run Nos. 4, 6 and 7 employed a hydroformylation catalyst solution containing 540 ppm rhodium, 10% by weight TPP, 30% by weight butyraldehyde and the balance aldehyde condensation by-products; run number 9 employed a hydroformylation catalyst solution containing 635 ppm rhodium, 12% by weight TPP, 30% by weight butyraldehyde, 20% by weight hexane, 10% by weight C$_9$ aldehyde and the balance butyraldehyde condensation by products; run numbers 5 and 10 employed as the non-polar feed material the organic solutions recovered from the extraction column in prior run numbers 4 and 9 respectively, and run number 10 employed a hydroformylation catalyst solution containing 312 ppm rhodium, 10% by weight TPP, 80% by weight butyraldehyde and aldehyde condensation by-products.

TABLE 9

| Run No. | O/A | Extraction Eff. (%) | Rh Balance (%) |
|---|---|---|---|
| 1 | 3.8 | 63.5 | 94 |
| 2 | 7.0 | 58.4 | 92 |
| 3 | 10.1 | 30.9 | 91 |

TABLE 10

| Run No | Catalyst Activity (%) | O/A | TPPMS-Na (wt %) | Extraction Eff. (%) | Rh Balance |
|---|---|---|---|---|---|
| 4 | 35 | 10.8 | 5.0 | 21.0 | 95 |
| 5 | — | 3.3 | 5.0 | — | 95 |
| 6 | 35 | 3.0 | 5.0 | 46.2 | 97 |
| 7 | 35 | 3.0 | 2.5 | 30.3 | 102 |
| 8 | 39 | 4.0 | 2.5 | 5.8 | 109 |
| 9 | 35 | 3.5 | 5.0 | 104.0 | 87 |
| 10 | — | 3.5 | 5.0 | — | 99 |
| 11 | 95 | 3.5 | 5.0 | 92 | 102 |

EXAMPLE 28

This example illustrates the continuous extraction of rhodium from an aqueous (polar) solution containing 5% by weight TPPMS-Na ligand and 382 ppm rhodium. This aqueous solution corresponds to the aqueous stream recovered from run number 11 reported in Table 10. The same equipment employed in Example 27 was used. The aqueous solution first was treated with maleic acid to convert completely the TPPMS-Na ligand to a non-coordinating form. An isobutyraldehyde solution containing 10% by weight triphenylphosphine then was used as the non-polar extractant. An extraction efficiency of 83.0% was obtained.

EXAMPLES 29 and 30

These examples demonstrate the ability of an aqueous (polar) solution of the sodium salt of DIPHOS-monosulfonic acid (bisdiphenylphosphinoethane m-monosulfonic acid, sodium salt) (S-DIPHOS-Na) to extract rhodium from hydroformylation reaction medium. Both a fresh catalyst solution containing 10% by weight triphenylphosphine, 179 ppm rhodium and the balance tridecanal and a used catalyst of unknown activity containing 635 ppm of rhodium, 12% triphenylphosphine ligand, 30% by weight butyraldehyde, 20% by weight hexane, 10% by weight C$_9$ aldehyde and the balance butyraldehyde condensation by-products were treated with the aqueous solution. In each example, one part by weight of the organic solution was contacted for several minutes with one part by weight of an aqueous solution containing 2% by weight of the sulfonated DIPHOS. An analysis of the aqueous extractant revealed that 89% of the rhodium in the fresh catalyst and 25% of the rhodium in the used catalyst were recovered in the aqueous phase used to contact the fresh and used catalyst solutions respectively.

EXAMPLE 31

This example illustrates the use of a chemical reagent to improve the extraction of rhodium from a non-polar organic solution. Spent hydroformylation catalyst solution having an activity of about 35% and containing about 22 wt % triphenylphosphine (non-polar solvent-soluble and polar solvent-insoluble ligand), about 750 ppm rhodium, about 11% by weight butyraldehyde and the balance aldehyde condensation by-products was treated with allyl chloride to examine its effect on extraction efficiency. The results are presented in Table 11.

TABLE 11

| grams allyl chloride per kilogram catalyst solution | Treatment Time (hrs) | Treatment Temp. (°C.) | Rh Extraction (%) |
|---|---|---|---|
| 2.6 | 4 | 60 | 85 |
| 4 | 1 | 25 | 35 |
| 10 | 1 | 100 | 83 |
| 10 | 16 | 100 | 72 |

EXAMPLE 32

The following example illustrates the effect of the relative amount of non-polar organic solvent-soluble and polar solvent-insoluble ligand in the non-polar phase to the relative amount of polar solvent-soluble ionic ligand in the polar phase on the distribution or partitioning of rhodium between the two phases. In these examples, fresh hydroformylation catalyst solutions (non-polar organic solutions) containing 300 ppm rhodium were prepared by mixing rhodium dicarbonyl acetylacetonate in Texanol ® with an amount of non-polar solvent-soluble ligand to yield the molar concentrations of ligand noted below. Before conducting the various extractions, the fresh catalyst solutions were activated (conditioned) by using them for 24 hours in a continuously operating hydroformylation reactor hydroformylating propylene to butyraldehyde.

Catalyst solutions were prepared using triphenylphosphine (TPP) in a molar concentration of about 0.324 mol/liter; cyclohexyldiphenylphosphine (CHDPP) in molar concentrations of about 0.032, 0.095, 0.13 and 0.15 mol/liter; n-butyldiphenylphosphine (BDPP) in molar concentrations of about 0.07 and 0.14 mol/liter and bisdiphenylphosphinoethane (DIPHOS) in molar concentrations of about 0.02, 0.06, 0.11 and 0.21 mol/liter.

Polar extractants were prepared by making aqueous solutions of the following ionic ligands in a variety of molar concentrations: the sodium salt of triphenylphosphine monosulfonate (TPPMS-Na) molar concentrations from about 0.002 to 0.3 mol/liter; the sodium salt of triphenylphosphine trisulfonate (TPPTS-Na) molar concentrations from about 0.002 to 0.1 mol/liter and the sodium salt of monosulfonated bisdiphenylphosphinoethane (S-DIPHOS-Na) at a molar concentration of 0.02 mol/liter. Extractions were performed by shaking equal amounts of non-polar organic solutions and the polar (aqueous) solutions in standard laboratory glassware for four hours and then separating the non-polar and polar phases via centrifugation.

The results are reported below in Tables 12 through 20, which illustrate the ratio of the rhodium concentration in the organic phase to the rhodium concentration in the aqueous phase after extraction (Rh ratio (O/A)) as a function of the particular ligands and the ratio of non-polar solvent-soluble ligand (non-polar ligand) to polar solvent-soluble ionic ligand (ionic ligand) in the two phases. Conditions yielding low Rh ratios (less than 1.0) favor extraction into the polar (aqueous) phase, while conditions yielding higher Rh ratios (greater than 1.0) favor extraction into the non-polar organic phase. The results are also plotted in FIGS. 2 through 5.

TABLE 12
TPP and TPPMS-Na

| Molar Ratio Non-Polar ligand to Ionic Ligand | Rh Ratio (O/A) |
|---|---|
| 1.2 | 0.04 |
| 2.4 | 0.04 |
| 3.0 | 0.05 |
| 3.9 | 0.05 |
| 5.9 | 0.06 |
| 11.8 | 0.11 |
| 23.6 | 0.82 |
| 23.6 | 6.2 |
| 39.4 | 10.2 |
| 59.0 | 31.5 |

TABLE 13
TPP and TPPTS-Na

| Molar Ratio Non-Polar ligand to Ionic Ligand | Rh Ratio (O/A) |
|---|---|
| 3.7 | 0.77 |
| 6.1 | 0.90 |
| 36.8 | 3.7 |
| 73.7 | 12.1 |

TABLE 14
CHDPP and TPPMS-Na

| Molar Ratio Non-Polar ligand to Ionic Ligand | Rh Ratio (O/A) |
|---|---|
| 0.23 | 0.24 |
| 0.38 | 0.47 |
| 0.69 | 0.25 |
| 1.2 | 0.42 |
| 11.5 | 1.1 |
| 15.4 | 4.4 |
| 23.1 | 10.2 |
| 46.2 | 17.5 |

TABLE 15
CHDPP and TPPTS-Na

| Molar Ratio Non-Polar ligand to Ionic Ligand | Rh Ratio (O/A) |
|---|---|
| 0.36 | 1.0 |
| 0.60 | 0.77 |
| 1.1 | 0.80 |
| 1.8 | 0.80 |
| 21.6 | 3.0 |
| 54.0 | 4.9 |

TABLE 16
BDPP and TPPMS-Na

| Molar Ratio Non-Polar ligand to Ionic Ligand | Rh Ratio (O/A) |
|---|---|
| 0.51 | 0.19 |
| 0.85 | 0.45 |
| 1.0 | 0.68 |
| 1.7 | 0.83 |
| 10.2 | 6.3 |
| 12.8 | 22.4 |
| 20.4 | 30.2 |

TABLE 17
BDPP and TPPTS-Na

| Molar Ratio Non-Polar ligand to Ionic Ligand | Rh Ratio (O/A) |
|---|---|
| 0.80 | 0.28 |
| 1.3 | 0.53 |
| 1.6 | 0.65 |
| 2.7 | 1.1 |
| 10.0 | 4.2 |
| 16.0 | 4.9 |

TABLE 18
DIPHOS and TPPMS-Na

| Molar Ratio Non-Polar ligand to Ionic Ligand | Rh Ratio (O/A) |
|---|---|
| 0.16 | 13.0 |
| 0.26 | 21.1 |
| 0.47 | 14.2 |
| 0.78 | 34.6 |

TABLE 19
DIPHOS and TPPTS-Na

| Molar Ratio Non-Polar ligand to Ionic Ligand | Rh Ratio (O/A) |
|---|---|
| 0.24 | 26600 |
| 0.40 | 30200 |
| 0.73 | 227 |
| 1.2 | 818 |

TABLE 20
DIPHOS and S-DIPHOS-Na

| Molar Ratio Non-Polar ligand to Ionic Ligand | Rh Ratio (O/A) |
|---|---|
| 1.1 | 37.4 |
| 5.3 | 65.5 |
| 10.7 | 34.1 |

EXAMPLE 33

A 10 gram sample of a fresh hydroformylation catalyst solution (100% activity) containing 300 ppm of rhodium, 1.5% by weight tribenzylphosphine ligand and the balance Texanol ® was contacted once with 5.0 grams of a 5% by weight aqueous (polar) solution of TTPMS-Na ionic ligand. The analysis of the aqueous wash showed that 67% of the rhodium was recovered in the aqueous phase.

While the present invention has particular applicability for the recovery and reuse of non-polar organic solvent-soluble rhodium-ligand coordination complex from non-polar organic solutions used for the hydroformylation of higher olefins, and particularly for solutions which may have become uneconomical for further use due to the accumulation of high boiling aldehyde condensation by-products, those skilled in the art will recognize that the invention can be used broadly for recovering Group VIII transition metals from any non-polar organic solution containing a non-polar organic solvent-soluble and polar solvent-insoluble coordination complex of the transition metal and free non-polar organic solvent-soluble organophosphorus ligand whether the driving force for recovery happens to be the presence or accumulation of some hard-to-remove by-product from the organic solution, a gradual deactivation of the catalyst or some other event.

Thus, while certain specific embodiments of the invention have been described with particularity herein, it will be recognized that various modifications thereof will occur to those skilled in the art and it is to be understood that such modifications and variations are to be included within the purview of this application and the spirit and scope of the appended claims.

We claim:

1. A method for recovering Group VIII transition metal from a substantially non-polar organic solution containing non-polar organic solvent-soluble and polar solvent-insoluble coordination complex of the Group VIII transition metal and a non-polar organic solvent-soluble and polar solvent-insoluble organophosphorus ligand, which comprises contacting such non-polar organic solution with a polar solution containing polar solvent-soluble ionic organophosphine ligand capable of forming a coordination complex with the transition metal, and transferring said Group VIII transition metal from said organic solution into said polar solution, and wherein said polar solution is selected from the class consisting of water, methanol, mixtures thereof, and solutions made therefrom.

2. The method of claim 1 wherein said organic solution contains free non-polar organic solvent-soluble and polar solvent - insoluble organophosphorus ligand.

3. The method of claim 2 wherein said Group VIII transition metal is rhodium.

4. The method of claim 3 wherein said polar solution is an aqueous solution.

5. A method for recovering rhodium from a substantially non-polar organic solution containing non-polar organic solvent-soluble and polar solvent-insoluble coordination complex of rhodium and a non-polar organic solvent-soluble and polar solvent-insoluble organophosphorus ligand comprising (a) contacting said non-polar organic solution with a polar solution selected from the class consisting of water, methanol, mixtures thereof, and solutions made therefrom, and containing polar solvent-soluble ionic organophosphine ligand capable of forming a coordination complex with the rhodium to transfer rhodium from said organic solution into the polar solution and (b) subsequently transferring said rhodium from the polar solution into a non-polar organic solvent containing organic solvent-soluble and polar solvent-insoluble organophosphorus ligand capable of forming a coordination complex with rhodium, by (i) treating the polar solution containing said transferred rhodium with a conditioning reagent selected from the group consisting of an ylid precursor, a strong acid, an lkylating agent, and an oxidizing reagent at a temperature of between about 0° C. to 250° C., for a sufficient period of time to reduce the amount of said polar solvent-soluble ionic organophosphine ligand capable of forming a coordination complex with the rhodium in the polar solution by at least about 70 percent; and (ii) contacting the polar solution produced in accordance with step (i) with a non-polar organic solvent containing non-polar organic solvent-soluble and polar solvent-insoluble organophosphorus ligand capable of forming a coordination complex with rhodium to transfer rhodium from said polar solution into said non-polar organic solvent.

6. The method of claim 5 wherein said polar solvent-soluble ionic organophosphine ligand is selected from compounds having the general formulae (1) and (2):

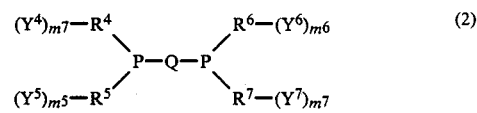

wherein $R^1$, $R^2$ and $R^3$ of formula (1) and $R^4$, $R^5$, $R^6$ and $R^7$ of formula (2) each individually represent a hydrocarbon radical containing from 1 to 30 carbon atoms selected from the group consisting of alkyl, aryl, alkaryl, aralkyl, and cycloalkyl radicals, where Q in formula (2) represents a divalent organic bridging group and where $Y^1$, $Y^2$ and $Y^3$ of formula (1) and $Y^4$, $Y^5$, $Y^6$ and $Y^7$ of formula (2) are substituted on the hydrocarbon radical and each individually represents an ionic radical of overall neutral charge selected from the group consisting of;

—$SO_3M$ wherein M represent inorganic or organic cationic atoms or radicals selected so that the ligand is polar solvent soluble, —$PO_3M$ wherein M represents inorganic or organic cationic atoms or radicals selected so that the ligand is polar solvent soluble, —$NR_3X'$ wherein each R represents a hydrocarbon radical containing from 1 to 30 carbon atoms selected from the class consisting of alkyl, aryl, alkaryl, aralkyl, and cycloakyl radicals, and X' represents inorganic or organic anionic atoms or radicals selected so that the ligand is polar solvent soluble, and —$CO_2M$ wherein M represents inorganic or organic cationic atoms or radicals selected so that the ligand is polar solvent soluble, wherein $m^1$, $m^2$ and $m^3$ of formula (1) and $m^4$, $m^5$, $m^6$ and $m^7$ of formula (2) are integers which can be the same or different and which can range from 0 to 5, and wherein at least one of $m_1$, $m_2$ and $m_3$ in formula (1) and at least one of $m_4$, $m_5$, $m_6$ and $m_7$ in formula (2) is equal to or greater than 1, sufficient to impart solubility in a polar solvent to the ligand.

7. The method of claim 6 wherein said ylid precursor is an unsaturated compound containing from 2 to 18 carbon atoms and is selected from the group consisting of compounds having the formula

wherein X is a radical selected from the group consisting of

—CN, —Cl, —Br, —I, —NO$_2$, and —OR$^{12}$; R$^{11}$ is a radical selected from the group consisting of hydrogen, alkyl, aryl, hydroxy, alkoxy, amino and halogen; R$^{12}$ is an alkyl or aryl radical; and R$^8$, R$^9$ and R$^{10}$ individually are radicals selected from the group consisting of hydrogen, alkyl, aryl, X radicals as defined above and —CH$_2$X radicals wherein X is the same as defined above; and wherein R$^8$ and R$^9$ taken together can form an alkylene group having from 2 to 8 carbon atoms; and anhydrides of the carboxylic acids of the unsaturated compounds within the scope of formula (A).

8. The method of claim 7 wherein said ylid precursor is maleic acid or maleic anhydride.

9. The method of claim 5 wherein said non-polar organic solvent-soluble and polar solvent-insoluble organophosphorus ligand is selected from the group consisting of triarylphosphines and cycloalkyldiarylphosphines.

10. The method of claim 9 wherein said polar solvent-soluble ionic organophosphine ligand is selected from the group consisting of ionic triarylphosphines and ionic bisdiarylphosphines.

11. The method of claim 9 wherein said triarylphosphine ligand is triphenylphosphine.

12. The method of claim 9 wherein said cycloalkyldiarylphosphine ligand is cyclohexyldiphenylphosphine.

13. The method of claim 10 wherein said ionic triarylphosphine is a sulfonated triphenylphosphine.

14. The method of claim 10 wherein said ionic bisdiarylphosphine is a sulfonated bisdiphenylalkylphosphine.

15. The method of claim 3 wherein said rhodium exhibits catalytic activity in hydroformylation.

16. The method of claim 15 wherein said polar solution is an aqueous solution.

17. A method for recovering rhodium from a substantially non-polar, hydroformylation reaction medium that contains non-polar organic solvent-soluble and polar solvent-insoluble coordination complex of rhodium and a non-polar organic solvent-soluble and polar solvent-insoluble organophosphorus ligand, free non-polar organic solvent-soluble and polar solvent-insoluble organophosphorus ligand and olefinic compound hydroformylation products which method comprises;

(a) contacting said hydroformylation reaction medium with a polar solution made selected from the class consisting of water, methanol, mixtures thereof, and solutions made therefrom, and containing polar solvent-soluble ionic organophosphine ligand capable of forming a coordination complex with the rhodium to transfer rhodium from said hydroformylation reaction medium into the polar solution;

(b) treating the polar solution containing said transferred rhodium with a conditioning reagent selected from the group consisting of an ylid precursor, a strong acid, an alkylating agent, and an oxidizing reagent at a temperature of between about 0° C. to 250° C. for a sufficient period of time to reduce the amount of said polar solvent-soluble ionic organophosphine ligand capable of forming coordination complex with rhodium in said polar solution by at least about 70 percent, and (c) contacting the polar solution produced in accordance with step (b) with a non-polar organic solvent containing non-polar organic solvent-soluble and polar solvent-insoluble organophosphorus ligand capable of forming a coordination complex with rhodium to transfer rhodium from said polar solution into said non-polar organic solvent.

18. The method of claim 17 wherein said polar solution is an aqueous solution.

19. An improvement in a continuous process for hydroformylating olefinic compounds of six to thirty carbon atoms in a hydroformylation reactor to form aldehydes by reacting the olefinic compound with hydrogen and carbon monoxide in the presence of a substantially non-polar hydroformylation reaction medium comprising a non-polar organic solution of a catalytic amount of a non-polar organic solvent-soluble and polar solvent-insoluble rhodium-organophosphorus ligand coordination complex catalyst and free non-polar organic solvent-soluble and polar solvent-insoluble organophosphorus ligand, said improvement comprising;

(a) contacting all or part of the hydroformylation reaction medium after its removal from the hydroformylation reactor, with a polar solution selected from the class consisting of water, methanol, mixtures thereof, and solutions made therefrom, and containing polar solvent-soluble ionic organophosphine ligand capable of forming a coordination complex with the rhodium to transfer rhodium from said hydroformylation reaction medium into the polar solution;

(b) subsequently, transferring said rhodium from the polar solution into a non-polar organic solvent containing non-polar organic solvent-soluble and polar solvent-insoluble organophosphorus ligand capable of forming a coordination complex with rhodium, by (i) treating the polar solution containing said transferred rhodium with a conditioning reagent selected from the group consisting of an ylid precursor, a strong acid, an alkylating agent, and an oxidizing reagent at a temperature of between about 0° C. to 250° C., for a sufficient period of time to reduce the amount of said polar solvent-soluble ionic organophosphine ligand capable of forming a coordination complex with the rhodium in the polar solution by at least about 70 percent; and (ii) contacting the polar solution produced in accordance with step (i) with a non-polar organic solvent containing non-polar organic solvent-soluble and polar solvent-insoluble organophosphorus ligand capable of forming a coordination complex with rhodium to transfer rhodium from said polar solution into said non-polar organic solvent; and (c) adding said non-polar organic solvent containing said transferred rhodium to the substantially non-polar hydroformylation reaction medium of said hydroformylation reactor.

20. A method for extracting rhodium in the form of a polar solvent-soluble coordination complex from a non-polar organic solution comprising polar solvent-insoluble, organically solubilized rhodium-nonionic organophosphorus ligand coordination complex, polar solvent-insoluble, organically solubilized free nonionic organophosphorus ligand, and non-polar organic solvent for said rhodium-ligand complex and said free ligand, which method comprises (1) mixing said organic solution with a polar solution selected from the class consisting of water, methanol, mixtures thereof, and solutions made therefrom, and containing a polar solvent-soluble ionic organophosphine ligand for sufficient period time in order to convert said polar solvent-insoluble rhodium complex into a polar solvent-soluble rhodium-ionic organophosphine coordination complex, and (2) recovering the polar solution of said polar solvent-soluble rhodium complex.

21. A method for recovering a Group VIII transition metal from a polar solution selected from the class consisting water, methanol, mixtures thereof, and solutions made therefrom, and containing a polar solvent-soluble coordination complex of a Group VIII transition metal and a polar solvent-soluble ionic organophosphine ligand comprising:

(i) treating the polar solution with a conditioning reagent selected from the group consisting of a ylid precursor, a strong acid, an alkylating agent, and an oxidizing reagent at a temperature of between about 0° C. to 250° C., for a sufficient period of time to reduce the amount of said polar solvent-soluble ionic organophosphine ligand capable of forming a coordination complex with the rhodium in the polar solution by at least about 70 percent; and (ii) contacting the polar solution produced in accordance with step (i) with a non-polar organic solvent containing non-polar organic solvent-soluble and polar solvent-insoluble organophosphorus ligand capable for forming a coordination complex with rhodium to transfer rhodium form said polar solution into said non-polar organic solvent.

22. The method of claim 21 wherein said ylid precursor is an unsaturated compound containing from 2 to 18 carbon atoms and is selected from the group consisting of compounds having the formula

(A)

wherein X is a radical selected from the group consisting of

$-CN$, $-Cl$, $-Br$, $-I$, $-NO_2$, and $-OR^{12}$; $R^{11}$ is a radical selected from the group consisting of hydrogen, alkyl, aryl, hydroxy, alkoxy, amino and halogen; $R^{12}$ is an alkyl or aryl radical; and $R^8$, $R^9$ and $R^{10}$ individually are radicals selected from the group consisting of hydrogen, alkyl, aryl, X radicals as defined above and $-CH_2X$ radicals wherein X is the same as defined above; and wherein $R^8$ and $R^9$ taken together can form an alkylene group having from 2 to 8 carbon atoms; and anhydrides of the carboxylic acids of the unsaturated compounds within the scope of formula (A).

23. The method of claim 22 wherein said ylid precursor is maleic acid or maleic anyhdride.

24. The method of claim 21 wherein said non-polar organic solvent-soluble and polar solvent-insoluble organophosphorus ligand is selected from the group consisting of triarylphosphines and cycloalkyldiarylphosphines.

25. The method of claim 24 wherein said polar solvent-soluble ionic organophosphine ligand is selected from the group consisting of ionic triarylphosphines and ionic bisdiarylphosphines.

26. The method of claim 24 wherein said triarylphosphine ligand is triphenylphosphine.

27. The method of claim 24 wherein said cycloalkyldiarylphosphine ligand is cyclohexyldiphenylphosphine.

28. The method of claim 25 wherein said ionic triarylphosphine is a sulfonated triphenylphosphine.

29. The method of claim 25 wherein said ionic bisdiarylphosphine is a sulfonated bisdiphenylalkylphosphine.

* * * * *